United States Patent
Baud et al.

(10) Patent No.: US 11,067,585 B2
(45) Date of Patent: Jul. 20, 2021

(54) METHOD FOR MONITORING CANCER AND/OR INFLAMMATORY REACTION BASED ON RELB PHOSPHORYLATION

(71) Applicants: CENTRE NATIONAL DE LA RECHERCHE SCIENTIFIQUE (CNRS), Paris (FR); UNIVERSITE PARIS DESCARTES, Paris (FR); INSTITUT NATIONAL DE LA SANTE ET DE LA RECHERCHE MEDICALE (INSERM), Paris (FR)

(72) Inventors: Veronique Baud, Paris (FR); Katy Billot, Bourg la Reine (FR)

(73) Assignees: CENTRE NATIONAL DE LA RECHERCHE SCIENTIFIQUE (CNRS), Paris (FR); UNIVERSITE PARIS DESCARTES, Paris (FR); INSTITUT NATIONAL DE LA SANTE ET DE LA RECHERCHE MEDICALE (INSERM), Paris (FR)

(*) Notice: Subject to any disclaimer, the term of this patent is extended or adjusted under 35 U.S.C. 154(b) by 200 days.

(21) Appl. No.: 15/817,868

(22) Filed: Nov. 20, 2017

(65) Prior Publication Data
US 2018/0156819 A1 Jun. 7, 2018

Related U.S. Application Data

(62) Division of application No. 14/784,484, filed as application No. PCT/EP2014/058021 on Apr. 18, 2014, now Pat. No. 9,851,363.

(30) Foreign Application Priority Data

Apr. 18, 2013 (EP) .................................... 13305508

(51) Int. Cl.
C07K 16/18 (2006.01)
G01N 33/68 (2006.01)
G01N 33/574 (2006.01)

(52) U.S. Cl.
CPC ......... *G01N 33/6872* (2013.01); *C07K 16/18* (2013.01); *G01N 33/57484* (2013.01); *G01N 2333/4703* (2013.01); *G01N 2440/14* (2013.01); *G01N 2500/04* (2013.01); *G01N 2500/10* (2013.01)

(58) Field of Classification Search
None
See application file for complete search history.

(56) References Cited

PUBLICATIONS

Anonymous: "Monoclonal Anti-Phosphoserine antibody produced in mouse", Sigma-Aldrich, XP002712027, Retrieved from the Internet: URL:http://www.sigmaaldrich.com/catalog/pr oduct/sigma/p3430?lang=en&region=NL [retrieved on Aug. 29, 2013].
M Neumann et al: "Glycogen synthase kinase-3[beta] is a crucial mediator of signal-induced RelB degradation", Oncogene, vol. 30, No. 21, May 26, 2011 (May 26, 2011), pp. 2485-2492.
H. J. Maier et al: "Critical Role of RelB Serine 368 for Dimerization and p100 Stabilization", Journal of Biological Chemistry, vol. 278, No. 40, Oct. 1, 2003 (Oct. 1, 2003), pp. 39242-39250.
Marienfeld Ralf et al: "Signal-specific and phosphorylation-dependent RelB degradation: A potential mechanism of NF-kappaB control", Oncogene, Nature Publishing Group, GB, vol. 20, No. 56, Dec. 6, 2001 (Dec. 6, 2001), pp. 8142-8147.
Christina W YDE et al: "NFi B signaling is important for growth of antiestrogen resistant breast cancer cells", Breast Cancer Research and Treatment, vol. 135, No. 1, Apr. 18, 2012 (Apr. 18, 2012), pp. 67-78.

*Primary Examiner* — Nelson B Moseley, II
(74) *Attorney, Agent, or Firm* — Arrigo, Lee, Guttman & Mouta-Bellum LLP

(57) ABSTRACT

The present Inventors demonstrated that the RelB subunit of NFκB plays a crucial role in promoting cell migration. More precisely, they identified that this pro-migratory activity is mediated by the activation of the NFκB pathway through RelB phosphorylation at serine 472. In a first aspect, the present invention proposes to monitor the activation of the NFκB pathway by following the phosphorylation status of said serine. Also, the present invention discloses methods and kits for prognosing the evolution of a disease involving cell migration in a subject—treated or not—suffering thereof, based on the detection of said RelB-S472 phosphorylation.

3 Claims, 12 Drawing Sheets

Figure 1:
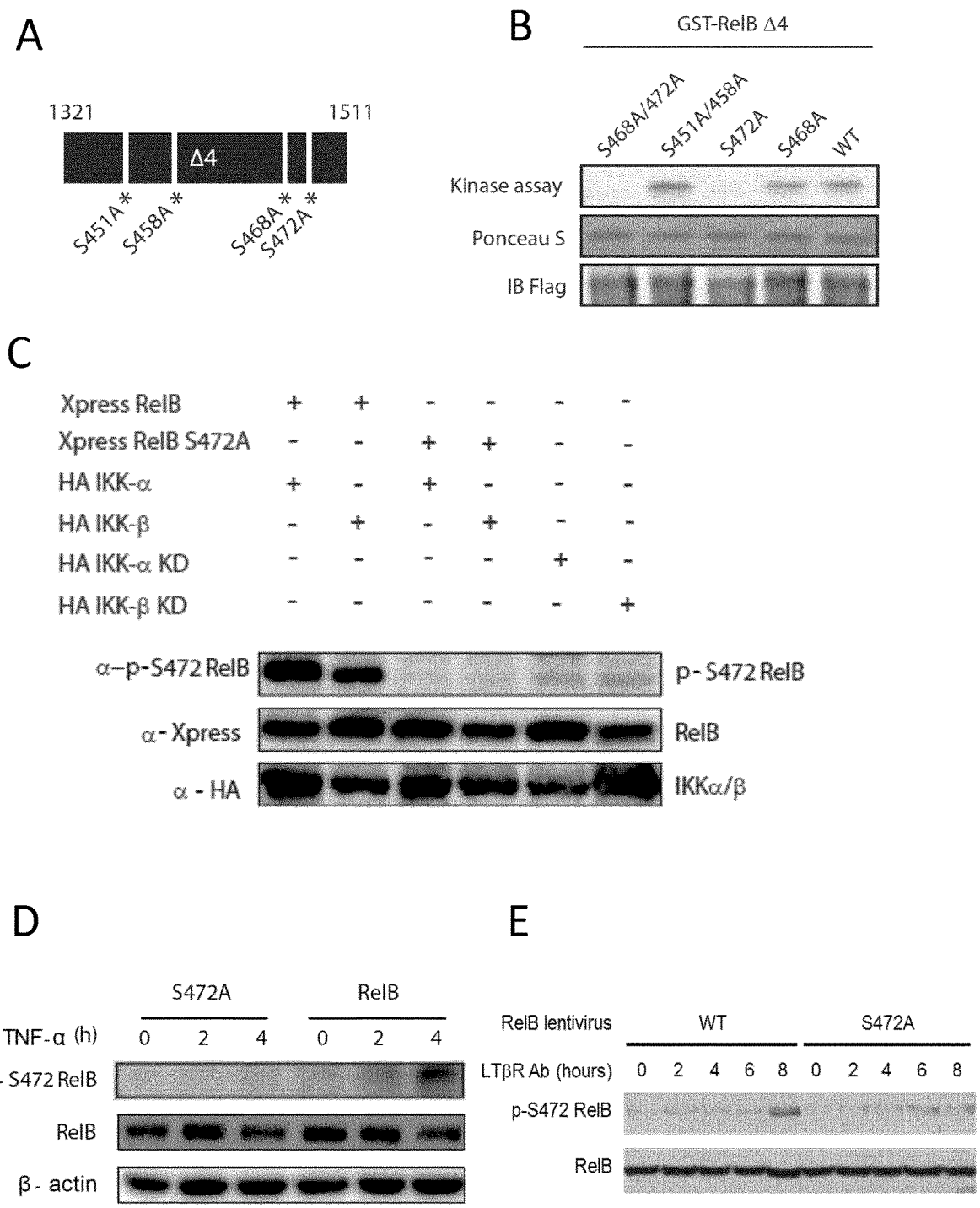

Specification includes a Sequence Listing.

B

A

B

A

MDA-MB-231 infected with lentivirus:

Empty vector (control)

WT RelB

RelB S472A

B

MDA-MB-231 p-S472 RelB
 RelB
 β-actin

METHOD FOR MONITORING CANCER AND/OR INFLAMMATORY REACTION BASED ON RELB PHOSPHORYLATION

BACKGROUND OF THE INVENTION

NFκB (nuclear factor kappa-light-chain-enhancer of activated B cells) is a protein complex that controls the transcription of DNA. NFκB is found in almost all animal cell types and is involved in cellular responses to stimuli such as stress, cytokines, free radicals, ultraviolet irradiation, oxidized LDL, and bacterial or viral antigens. It is now well accepted that the NF-κB pathway is involved in inflammatory diseases, cancer development and progression in human solid tumors.

In mammals, the NF-κB transcription factor family is composed of five members, RelA (p65), RelB, cRel (Rel), NF-κB1 (p50 and its precursor p105) and NF-κB2 (p52 and its precursor p100), and forms a collection of various homodimeric and heterodimeric complexes (Oeckinghaus A, et al, *Cold Spring Harb Perspect Biol.* 2009; Hayden M S and Ghosh S *Cell.* 2008).

The activity of the NF-κB subunit complexes is regulated by two major pathways. The first one, known as the classical or canonical NF-κB activation pathway, mainly applies to RelA:p50 dimers, which, under non-stimulated conditions, are sequestered in the cytoplasm through interactions with inhibitory proteins of the IκB family. Following stimulation with a broad range of stimuli such as TNF-α or IL-1, viruses, genotoxic agents and ionizing radiation, the IκB molecules are phosphorylated by the IκB kinase complex (IKK) at specific serine residues, leading to their ubiquitination and degradation by the proteasome pathway. RelA:p50 dimers are subsequently released and free to translocate to the nucleus where they activate transcription of various target genes (Ghosh, et al., *Cell* 2002). This pathway plays a major role in the control of innate immunity and inflammation (Baud, V. & Karin, M. *Trends Cell Biol* 2001; Bonizzi, G. & Karin, M. *Trends Immunol* 2004). The second pathway, the so-called alternative or non-canonical NF-κB signaling pathway, is stimulated by a more restricted set of cytokines that all belong to the TNF superfamily (e.g. BAFF, CD40L, LTβ). This pathway involves the upstream kinase NF-κB-inducing kinase (NIK) which activates IKKα, thereby leading to the phosphorylation and proteasome-dependent processing of p100, the main RelB inhibitor, resulting in RelB-p52 and RelB-p50 nuclear translocation and DNA binding (Derudder, E. et al. *J Biol Chem* 2003; Dejardin, E. et al. *Immunity* 2002; Xiao, G., et al, *Mol Cell* 2001; Coope, H. J. et al. *Embo J.* 2002; Claudio, E., et al. *Nat Immunol* 2002).

Most importantly, all studies point out to a crucial role for the RelB dependent alternative pathway in controlling the development, organization and function of secondary lymphoid organs and B-cell maturation and survival (Bonizzi, G. & Karin, M. *Trends Immunol* 2004; Dejardin, E. *Biochem Pharmacol.* 2006).

Beyond the alternative NF-κB signaling cascade, RelB-dependent DNA binding activity is negatively regulated at the nuclear level by several mechanisms, such as trapping in RelA/RelB or p100/RelB complexes, and specific serine phosphorylation (Marienfeld R, et al., *J Biol Chem* 2003; Jacque et al, PNAS 2005; Yilmaz Z B et al. Embo J 2003; Derudder E, et al. *J Biol Chem* 2003; Maier H J et al, *J Biol Chem* 2003). RelB containing dimers also display DNA binding specificity (Bonizzi G, et al. *Embo J* 2004; Fusco A J, et al., *EMBO* 2009; Natoli G and De Santa F, *Cell Death Differ* 2006), and RelB recruitment to some genes correlates with transcriptional down-regulation (IL12-p40), whereas in other cases (EBV-induced molecule 1 ligand chemokine (ELC) and macrophage-derived chemokine (MDC)), it increases transcriptional activity well over the level achieved by RelA or cRel (Saccani S, et al. *Mol Cell* 2003), further emphasizing the importance and unique role of RelB.

Several phosphorylation sites have been already characterized on the RelB protein. Phosphorylation at serine 368 has been shown to be required for NF-κB DNA binding activity, dimerization with other NF-κB subunits (p105/p50, p100/p52), and p100 half-life (Maier H J, et al., *J Biol Chem* 2003). Of note, no biological function has been associated to said phosphorylation and no inducer has been identified. Also, the threonine 84 and the serine 552 have been shown to undergo phosphorylation. This phosphorylation was found to be associated with the induction of RelB degradation by the proteasome in T cell lines (Marienfeld R, et al. *Oncogene* 2001). RelB is conserved through the mammal species and numerous homologs of the human RelB protein of SEQ ID NO:1 exist.

Activation of the canonical and non-canonical NFκB pathways has been involved in cell migration of a number of different cells.

For example, it has been shown that activation of the canonical NFκB pathway induces the expression of CXCR4 (Helbig et al, *J. Biol. Chem.* 2003) and the secretion of matrix metalloproteinases such as MMP9 (Sun et al, *Carcinogenesis,* 2012), so that it favors cancer cell migration and metastasis. Also, NFκB pathway activation has been shown to induce the secretion of MMP9 in macrophages (Rhee et al, *Journal of Biochemistry and Molecular Biology,* 2007) and to play a key role in regulating the immune response to infection. Finally, the NFκB pathway controls many genes involved in inflammation, and this pathway is found to be chronically active in many inflammatory diseases, such as inflammatory bowel disease, arthritis, sepsis, gastritis, asthma, atherosclerosis and others (Monaco et al, *PNAS* 2004). In view of all these implications, activation of the canonical NFκB pathway has been proposed to evaluate the clinical outcome of cancer patients, said activation being associated with a poor prognosis (Sun et al, *Carcinogenesis,* 2012). Also, inhibitors of the NF-κB pathway have been proposed to inhibit cancer cell migration, invasion, proliferation and tumor growth (Attoub et al, *Journal of Medical Sciences,* 2010) or inflammatory diseases (see anatabine, WO 2011/119722).

Interestingly, there are evidences indicating that the non-canonical NF-κB pathway and, in particular, the RelB subunit of NF-κB, is also involved in cell migration/invasion in a number of different cancer cells. This protein notably induces the more invasive mesenchymal phenotype in breast cancer cells (increase in snail, slug and vimentin protein expression along with a decrease in E-cadherin gene expression) (Wang et al, *Nat. Cell. Biol.* 2007). It has been also involved in invasion of gliomas (Lee, D. W., Et al., *PLoS One*) and prostate cancer (Guo, F., et al. *Mol Immunol* 2011).

FIGURE LEGENDS

FIG. 1 shows that IKK phosphorylates RelB at serine 472 upon TNFα treatment in vitro and in vivo. (A) Schematic representation of the GST-RelB (1321-1511 aa) C-terminal point mutants in which serine (S) was replaced by alanine is indicated. (B) Whole cell extracts from WT MEFS stimulated by TNFα were subjected to immunoprecipitation with anti-IKKα and IKK immunocomplex kinase assays were performed using as substrates GST-RelB point mutants (C) Whole cell extracts from HEK293 cells transiently transfected either with Xpress-WT RelB or Xpress-RelB S472A mutant along with HA-IKKα/β or kinase dead mutants (KD) were analyzed by immunoblotting for RelB serine-472 phosphorylation using our custom anti-RelB phospho-serine 472 antibody. (D) Whole cell extracts from RelB-deficient MEFs transduced with lentiviruses encoding either WT RelB (RelB) or S472A mutant (S472A), either untreated, or treated with TNFα for the indicated periods of time were analyzed by immunoblotting for RelB serine-472 phosphorylation as in (C). (E) Lymphotoxin β induces RelB serine-472 phosphorylation in fibroblasts. Whole cell extracts from RelB-deficient MEFs transduced with the indicated RelB lentiviruses, either untreated, or treated with agonistic LTβR agonistic antibody for the indicated periods of time were analyzed by immunoblotting for RelB serine-472 phosphorylation using anti-RelB phospho-serine 472 antibody.

Figure 2:
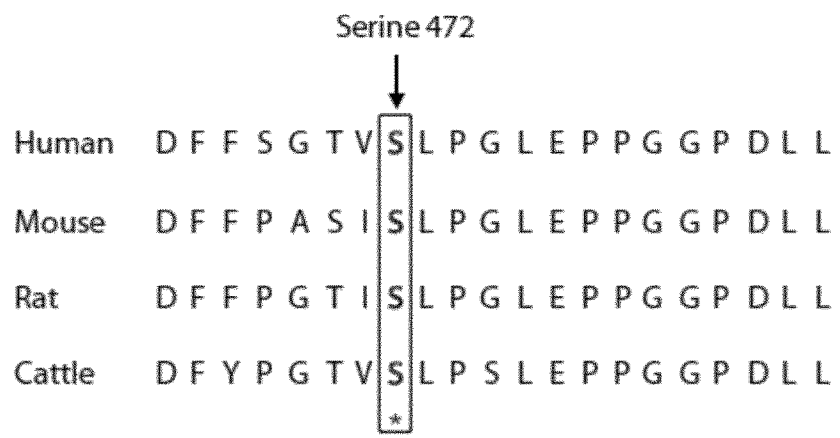

FIG. 2 shows equivalent sequences surrounding the 472 position of RelB in different animal species.

Figure 3:
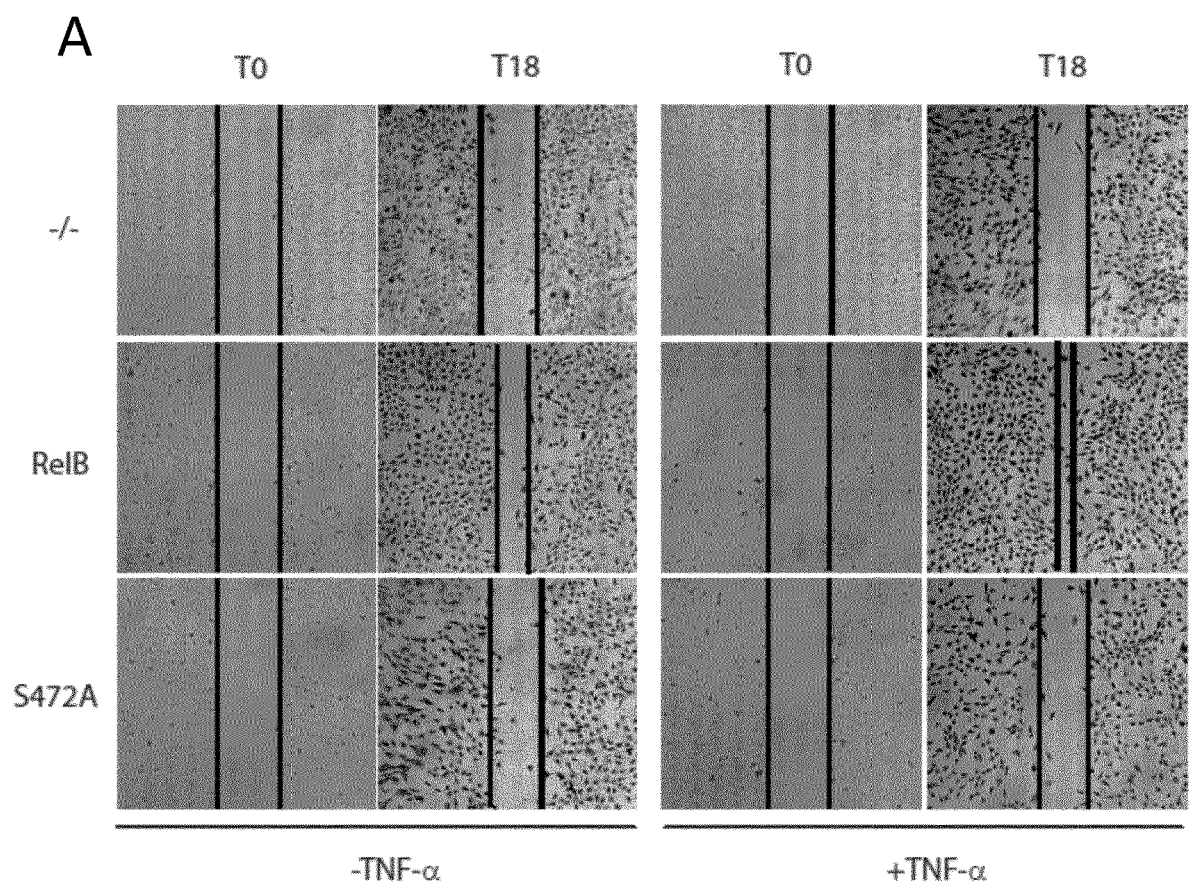
Figure 3:
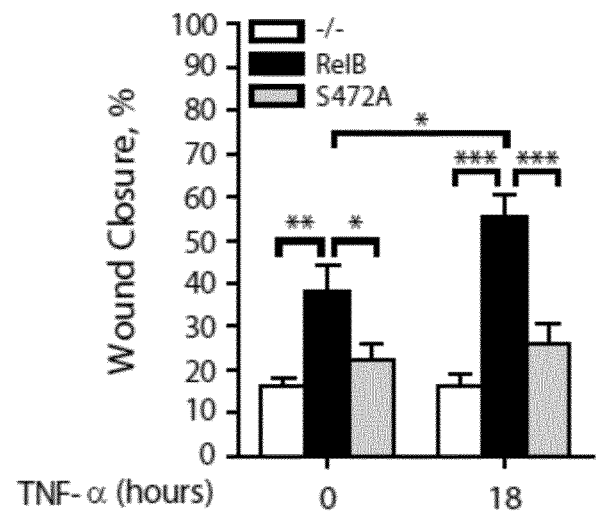

FIG. 3 shows impaired TNFα-induced migration in RelB S472A expressing MEFs. (A-B) RelB-deficient MEFs transduced with lentiviruses encoding either the parental empty vector (control), or WT RelB (RelB) or S472A (S472A) mutant were grown to confluence, serum-starved for 24 hours, treated with TNFα (30 ng/ml) for 18 hours or left untreated and analyzed for cell migration by scratch-wound assays as described in Experimental procedures. Wound closure of one representative experiment is shown (A) and the percentage (means+/−SEM of seven independent experiments for each cell line) of wound closure is represented in (B), *P<0.05; P<0.01; *P<0.001.

Figure 4:
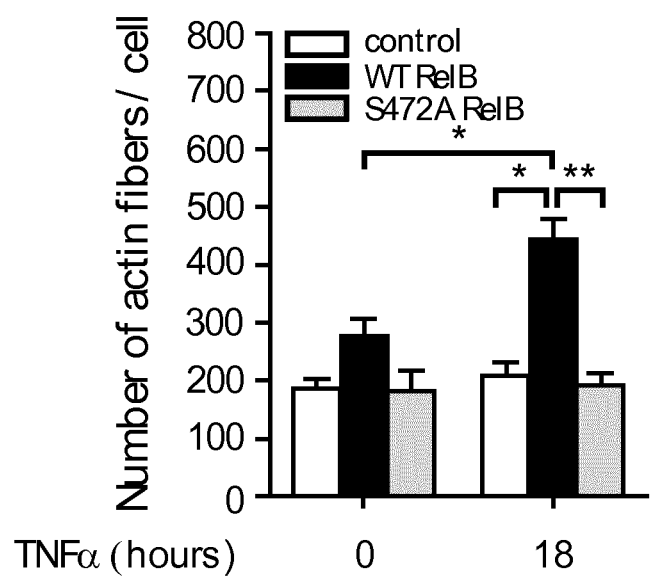

FIG. 4 shows that RelB mutation decreases filamentous actin fibers in the reconstituted relb$^{-/-}$ MEFs. Filamentous actin stress fibers from RelB-deficient MEFs transduced with the indicated lentiviruses and either left untreated or treated with TNFα for 18 hours were detected by fluorescence microscopy using rhodamine-conjugated phalloidin. Statistical analysis of the number of stress fibers/cell (means+/−SEM of three independent experiments for each cell line, at least thirty cells analyzed for each experiment) is represented, *P<0.05; P<0.01; *P<0.001.

Figure 5:
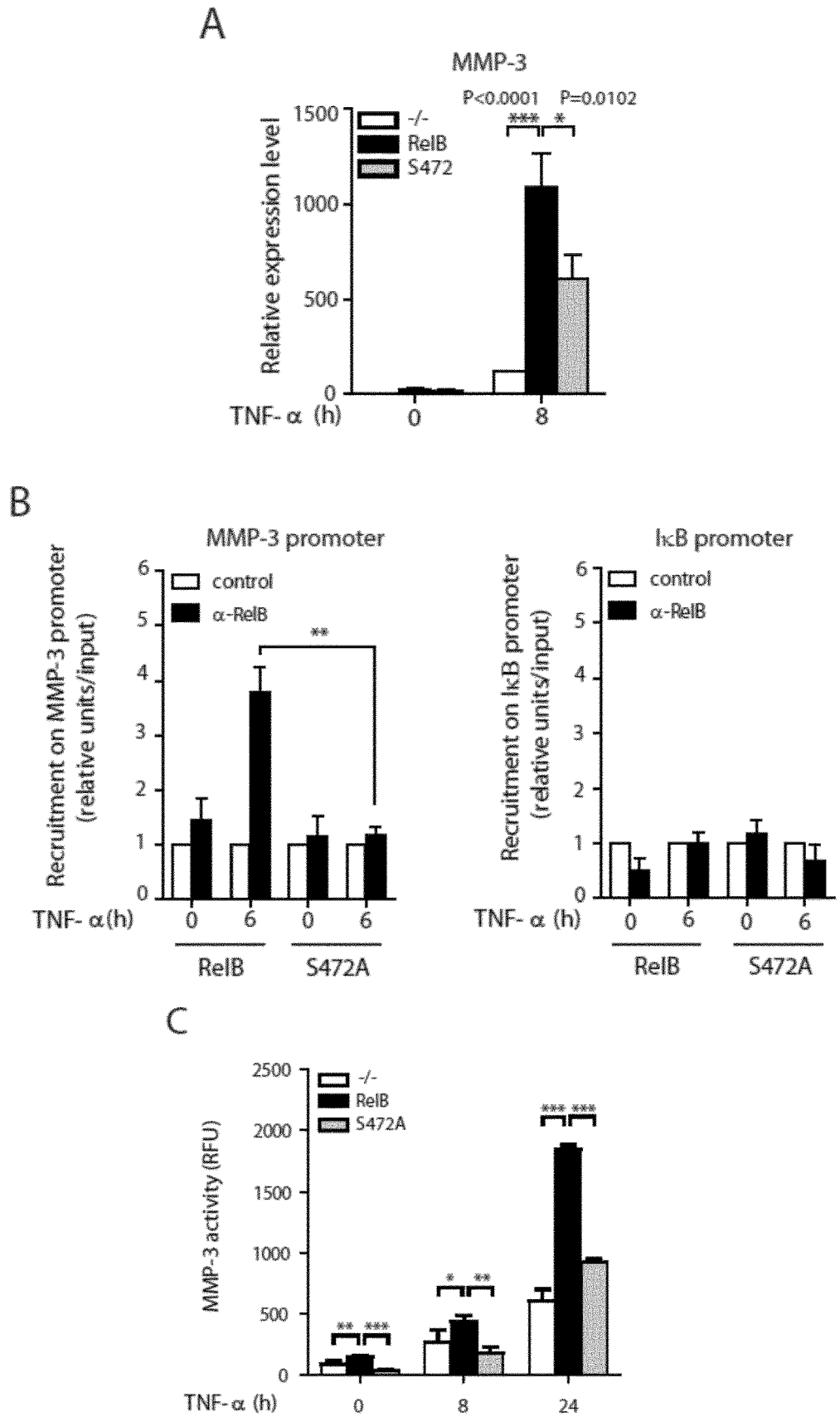
Figure 5:
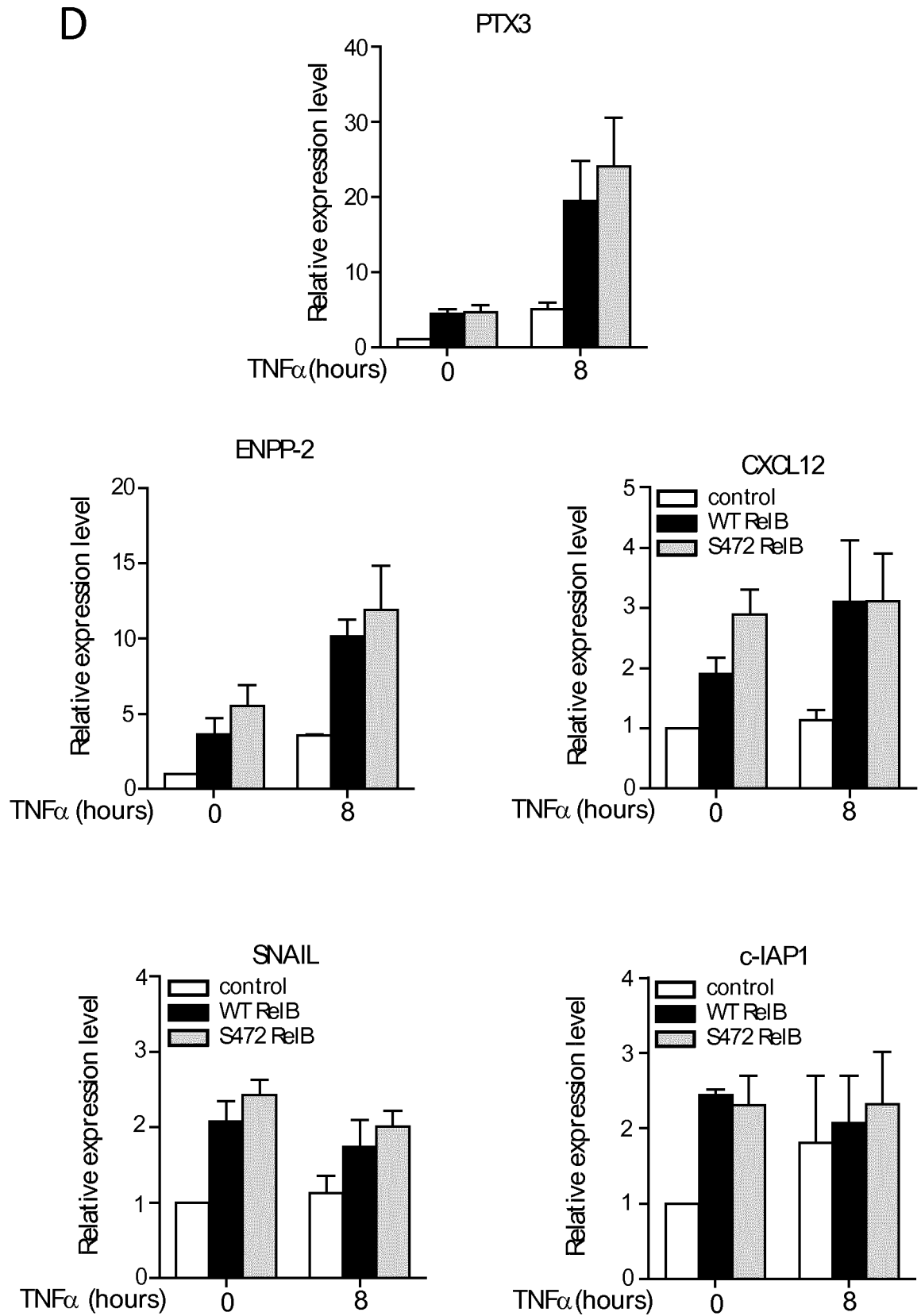

FIG. 5 shows that MMP-3 is a phospho-serine 472 specific RelB target gene.
(A) RelB S472A mutation prevents selective TNFα-induced pro-migration NF-κB target gene expression. Quantitative RT-PCR was performed with specific primer pairs for MMP3 gene using total RNAs prepared from RelB-deficient MEFs transduced with the indicated lentiviruses and treated with TNFα for 8 hours. Results are means±SEM (n=3) of three independent experiments normalized to the level of hypoxanthine-guanine phosphoribosyltransferase (HPRT) mRNA. *P<0.05; P<0.01; *P<0.001.
(B) TNFα-induced recruitment of RelB to the MMP-3 promoter depends on serine 472. Recruitment of WT RelB and S472 mutant to MMP-3 and IκB promoters was examined by ChIP assays followed by quantitative PCR analysis. The results are means±SEM of three independent experiments normalized to inputs that reflect relative amount of sonicated DNA fragments present before immunoprecipitation. **P<0.01.
(C) RelB serine-472 phosphorylation is critical for TNFα-induced MMP-3 activity. The activity of secreted MMP-3 was determined by fluorescent MMP-3 enzymatic assay. MMP-3 activity is represented as relative fluorescence units (RFU). The results are means±SEM (n=4). *P<0.05; P<0.01; *P<0.001.
(D) RelB S472A mutation has no effect on TNFα-induced NF-κB target gene expression. Quantitative RT-PCR was performed with specific primer pairs for the indicated genes using total RNAs prepared from RelB-deficient MEFs transduced with the indicated lentiviruses and treated with TNFα for 8 hours. Results are means±SEM (n=3) of three independent experiments normalized to the level of hypoxanthine-guanine phosphoribosyltransferase (HPRT) mRNA. *P<0.05; P<0.01; *P<0.001.

Figure 6:
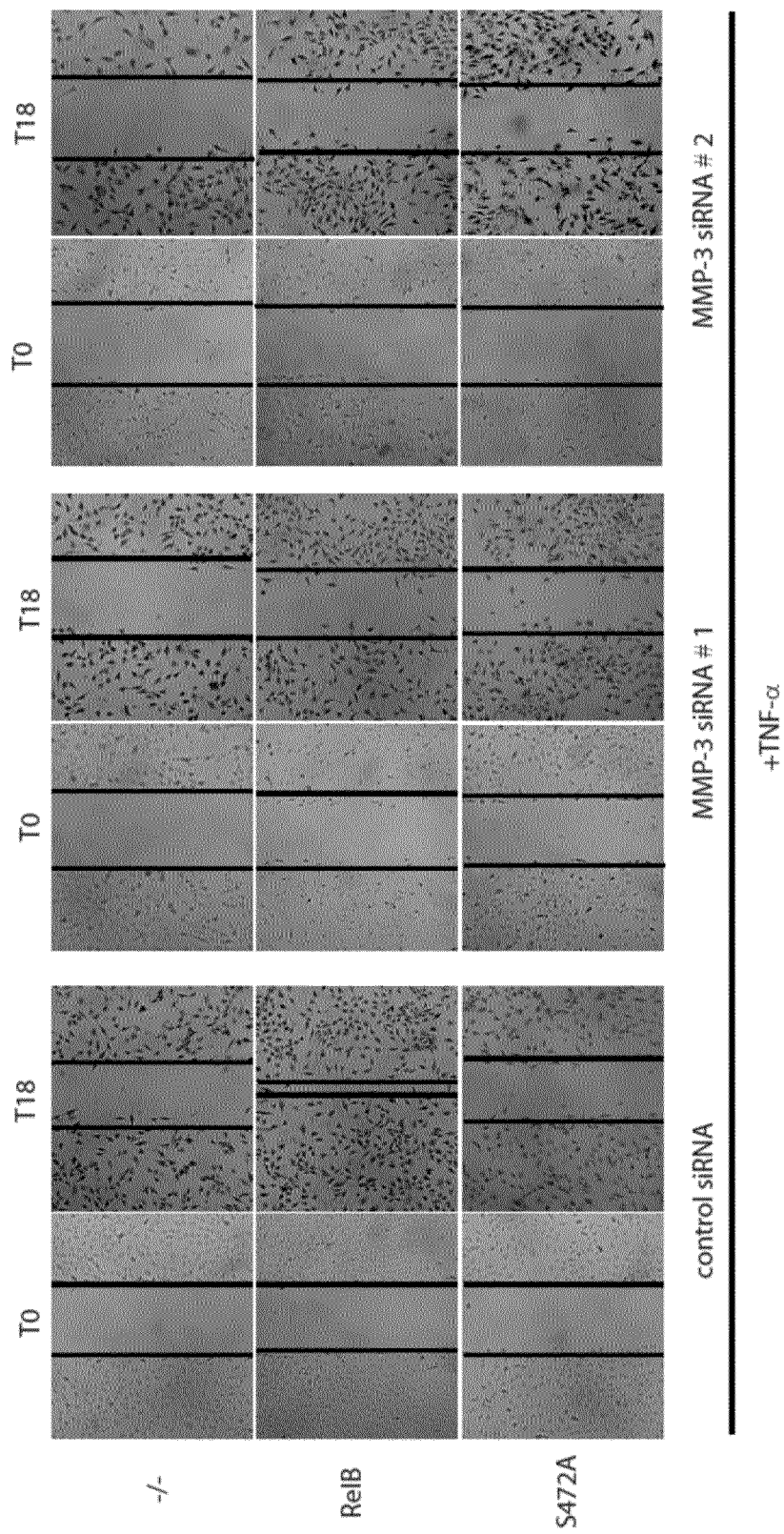
Figure 6:
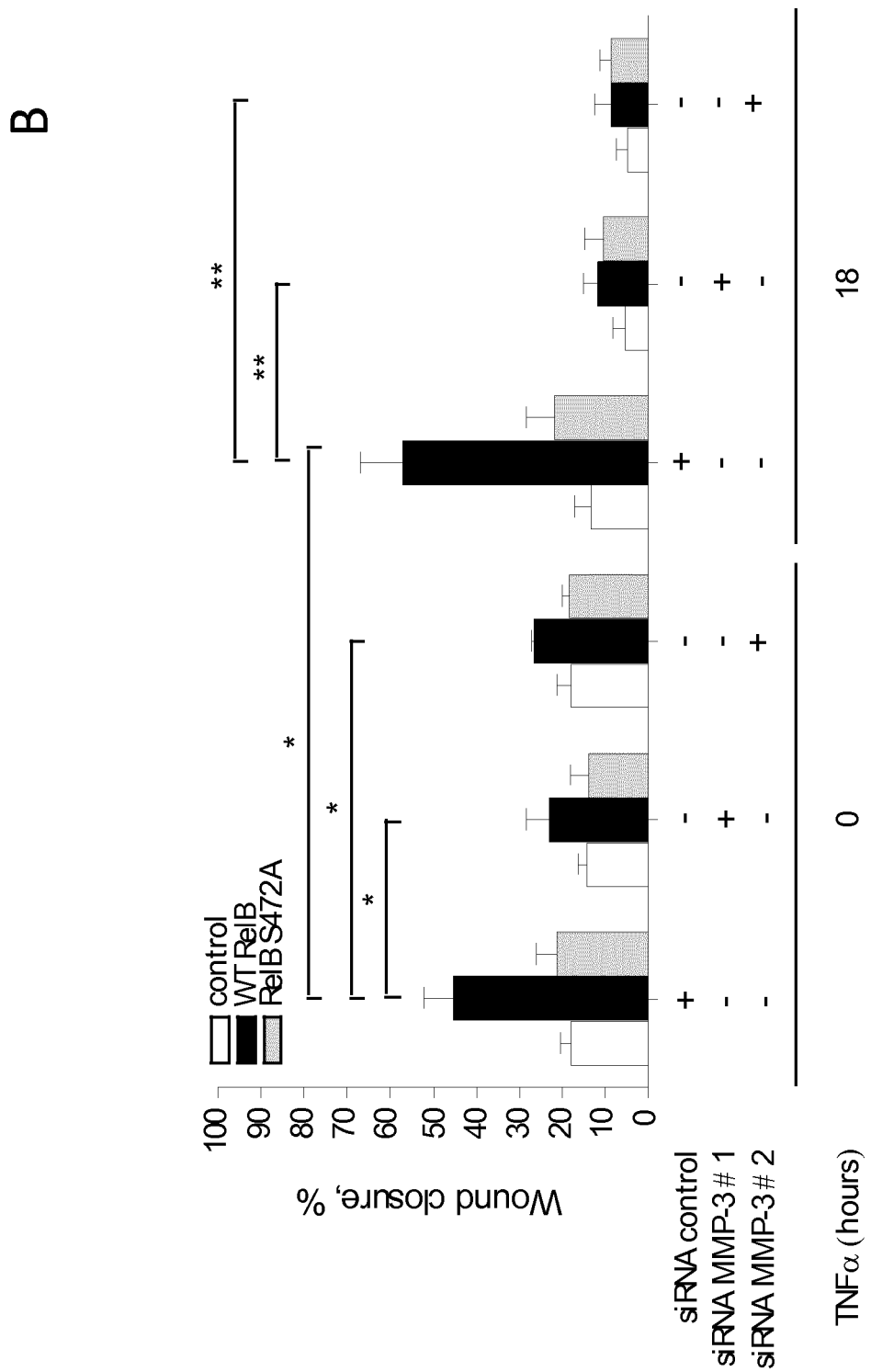

FIG. 6 shows that RelB serine 472 phosphorylation status promotes cell migration in a MMP-3 dependent manner.
MMP-3 knockdown by RNA interference inhibits RelB serine-472-mediated cell migration upon TNFα treatment. RelB-deficient MEFs transduced transduced with the indicated lentiviruses were transfected with either a scrambled control sequence (siRNA control) or two different siRNA oligonucleotides targeting MMP-3 (siRNA MMP-3 #1 or siRNA MMP-3 #2), grown to confluence, serum-starved for 24 hours, treated with TNFα for 18 hours or left untreated and analyzed for cell migration by scratch-wound assays at the time of insert removal (T0) and 18 h after insert removal (T18). Wound closure of one representative experiment upon TNFα treatment is shown (A) and the percentage (means+/−SEM of five independent experiments for each cell line) of wound closure is represented in (B), *P<0.05; P<0.01; *P<0.001.

Figure 7:
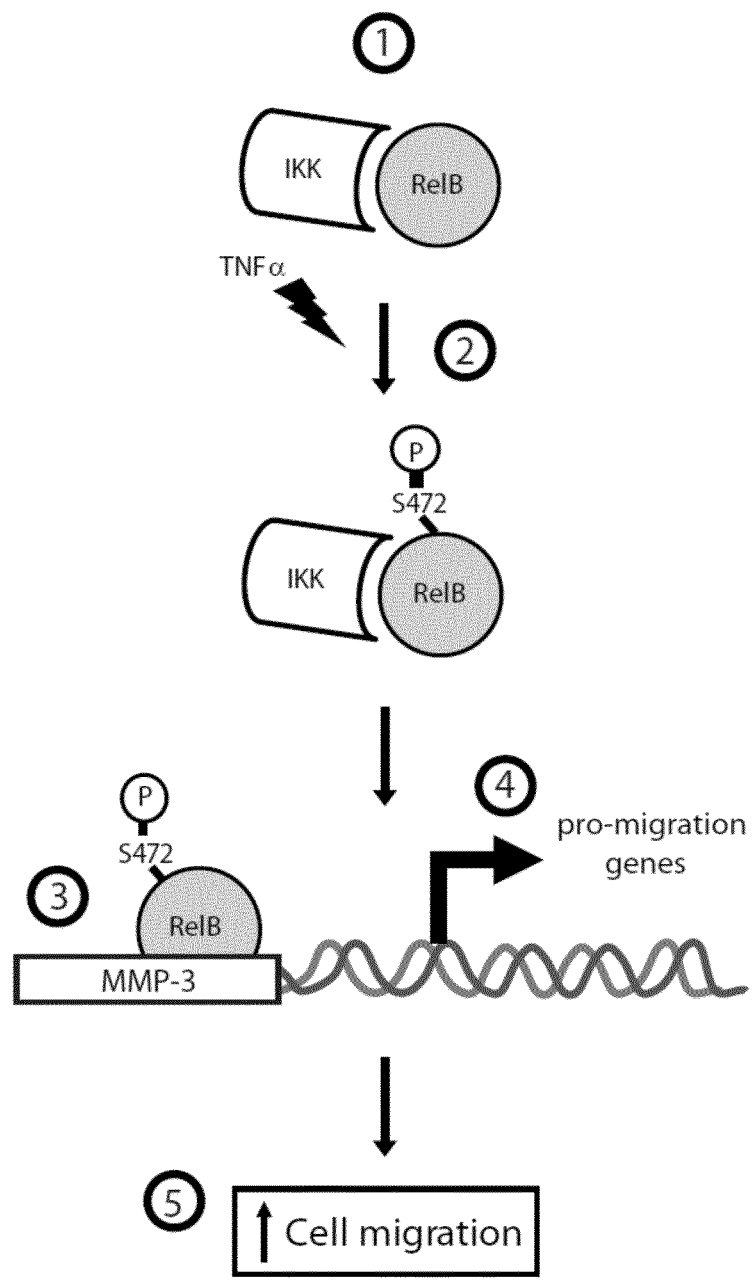

FIG. 7 discloses a schematic view of RelB serine-472 phosphorylation acting as an activator of cell migration. The IκB kinase (IKK) complex constitutively interacts with the RelB subunit of NF-κB (1). Activation of IKK upon prolonged TNFα treatment causes phosphorylation of RelB on serine-472 (2). It allows binding of RelB to the promoter of pro-migration genes such as MMP-3 (3), thereby resulting in selective NF-κB target gene expression involved in the control cell migration (4). TNFα-induced IKK-driven RelB serine-472 phosphorylation is subsequently required for efficient cell migration in an MMP-3-dependent manner (5).

Figure 8:
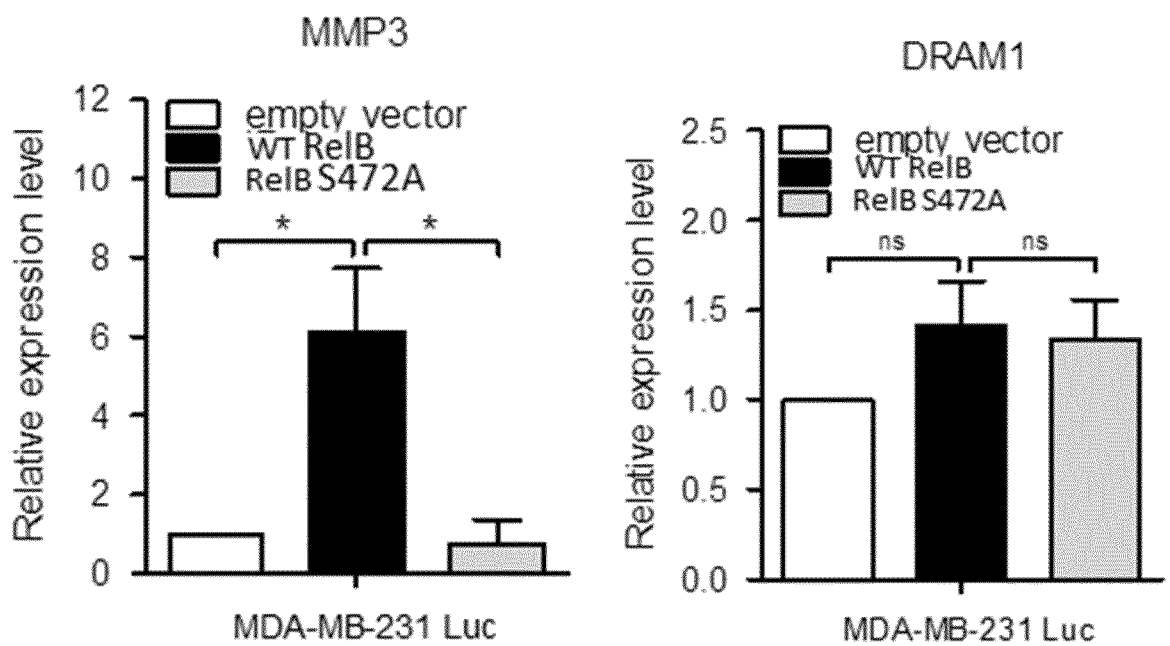
Figure 8:
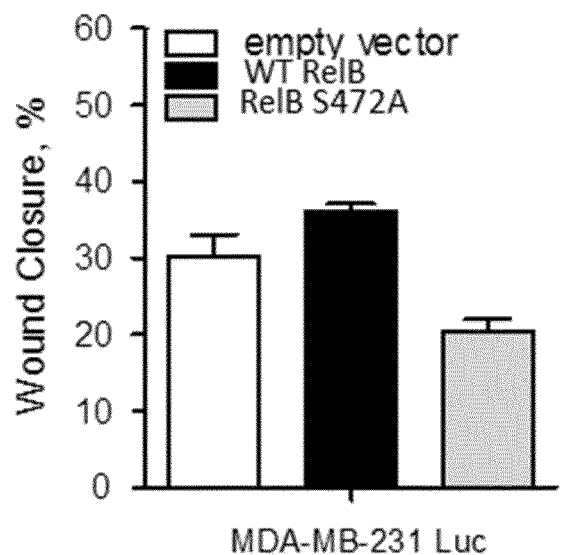

FIG. 8 shows that RelB exerts a serine-472-dependent activation of MMP3 expression in breast cancer cells and that RelB serine-472 phosphorylation status regulates RelB pro-migration function in breast cancer cells. (A) Quantitative RT-PCR was performed with specific primer pairs for the indicated genes using total RNAs prepared from MDA-MB-231 cells transduced with lentiviruses encoding either the parental empty vector (control) or WT RelB or RelB S472A mutant. Results are means±SEM of three independent experiments normalized to the level of hypoxanthine-guanine phosphoribosyltransferase (HPRT) mRNA. *P<0.05. (B) MDA-MB-231 cells transduced with lentiviruses encoding either the parental empty vector (control) or WT RelB or RelB S472A mutant, were grown to confluence, serum-starved for 24 hours, and analyzed for cell migration by scratch-wound assays as described in Materials and Methods.

Figure 9:
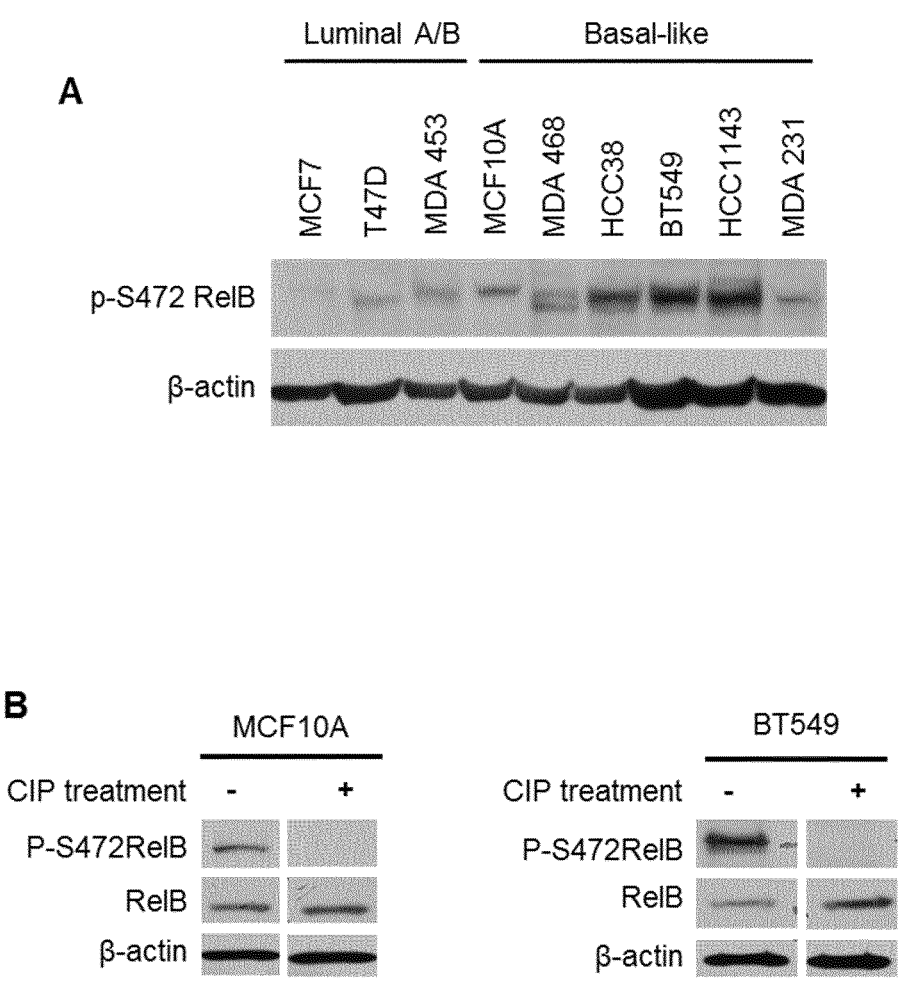

FIG. 9 shows that metastatic breast cancer cells exhibit RelB serine-472 phosphorylation that is not detectable in non-metastatic breast cancer cells. (A) Highest level of RelB serine-472 phosphorylation in highly aggressive basal-like human breast cancer cells in comparison to luminal A and B breast cancer cells. Whole cell extracts from either invasive basal-like (MCF10A, MDA-MB-468, HCC38, BT549, HCC1143 and MDA-MB-231) or luminal A and B (MCF7, T47D, MDA-MB-453) human breast cancer cells were analyzed by immunoblotting for the indicated proteins. (B)

Demonstration of the specificity of RelB in its phosphorylated state in metastatic breast cancer cells. Whole cell extracts of either MCF10A (left panels) or BT549 (right panels) metastatic breast cancer cells separated by SDS-PAGE and transferred to nitrocellulose membrane were either left untreated or treated with calf intestinal phosphatase (CIP) for one hour at 37° C. and analyzed by immunoblotting for the indicated proteins.

Figure 10:
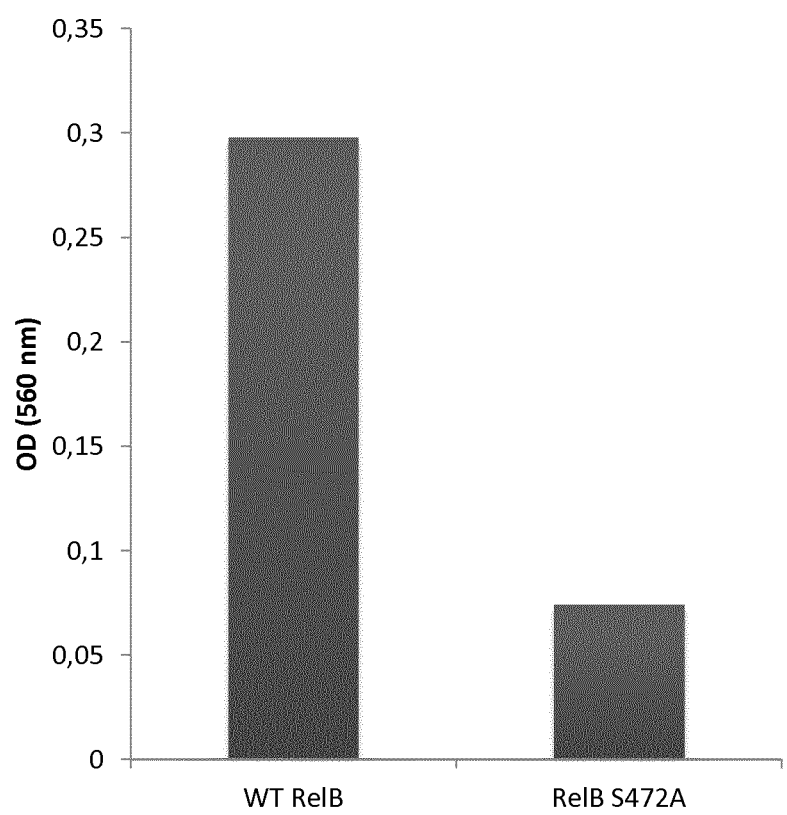

FIG. 10 discloses the results obtained by comparing migration of the WT RelB expressing cells and S472A mutants in transwells experiments.

Figure 11:
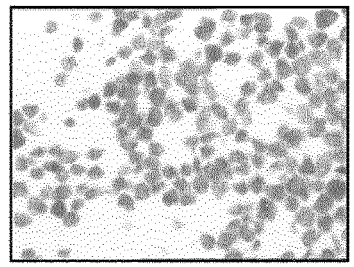
Figure 11:
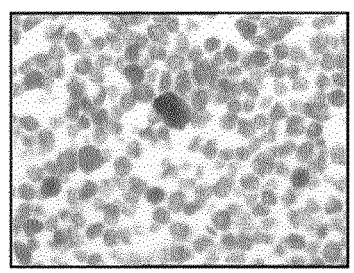
Figure 11:
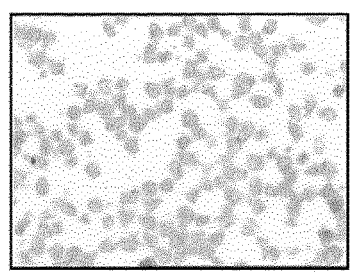
Figure 11:
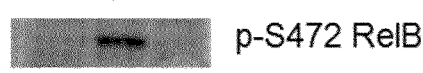
Figure 11:
Figure 11:

FIG. 11 shows the validation of the mouse anti-phospho serine-472 specific RelB monoclonal antibody by immunohistochemistry (IHC) and immunoblotting. (A) Validation of the mouse anti-phospho serine-472 specific RelB monoclonal antibody by immunohistochemistry (IHC) on MDA-MB-231 cells transduced with lentiviruses encoding either the parental empty vector (control) or WT RelB or RelB S472A mutant. (B) Validation of the mouse anti-phospho serine-472 specific RelB monoclonal antibody by immunoblotting on MDA-MB-231 cells transduced with lentiviruses encoding either the parental empty vector (control) or WT RelB or RelB S472A mutant.

DETAILED DESCRIPTION OF THE INVENTION

Several diseases involve undesired cell migration, including cancer, systemic lupus erythematosus (SLE), Sjogren's syndrome (SS), systemic sclerosis (SS), polymyositis, rheumatoid arthritis (RA), multiple sclerosis (MS), atherosclerosis, cerebral ischemia, abdominal aortic aneurysm (AAA), myocardial infarction (MI), cerebral amyloid angiopathy (CAA), angiogenesis, inflammation, and eczema. These diseases are the cause of loss of life and/or loss of the quality of life. While some therapeutic approaches have been successful, these diseases have not been completely eradicated. For example, cancer metastasis is responsible for 90% of treatment failure among cancer patients. To improve the life quality of patients suffering from said diseases, there is a significant need of more objective and accurate methods for analyzing the molecular mechanisms regulating the migratory capacity of target cells and the effectiveness of agents in inhibiting same. The ultimate goal is to determine the prognosis of said disease and adjust the treatment consequently so as to obtain the most acceptable therapeutic response. In a similar way, the said methods would enable a robust and easy following of a subject suffering from said disease. Eventually, the said methods would favor the development of novel treatment strategies to reduce diseases involving undesired cell migration, to improve the quality of life, and to prolong the survival of subjects suffering from these diseases.

As mentioned previously, determining the activation level of the NFκB pathway would be relevant to evaluate the clinical outcome of diseases involving undesired cell migration (e.g. cancer or inflammatory diseases).

Whereas expensive and time-consuming global evaluation of NF-κB activation by transcriptomics can be performed through the determination of mRNA levels of hundreds of genes whose expression was reported to be dependent on classical NF-κB pathway mainly involving its RelA subunit, there is currently no satisfactory reagent enabling to detect precisely and in a routine manner the activation status of the non-canonical NEκB pathway, and RelB in particular, in samples or in cells.

The present invention solves these needs by providing a robust and easy way to follow the activation of the RelB NF-κB subunit in a cell sample, as well as the means thereof.

As a matter of fact, the present Inventors demonstrate here for the first time that phosphorylation of RelB by the IκB kinase complex on a defined serine residue leads to RelB transcriptional activation. This activation is observed when cells are contacted with various stimuli, such as TNF-α or lymphotoxin-β.

Monitoring the phosphorylation status of RelB-serine 472 by appropriate reagents appears to be a reproducible and easy way to monitor the activation level of the RelB-dependent NEκB pathway.

The present Inventors also demonstrate for the first time that the RelB subunit of NEκB, once phosphorylated at serine 472, induces the migration of cells (and notably metastatic cancer cells), as serine-472 phosphorylated RelB binds to the endogenous promoter of migration-associated genes (e.g., MMP genes), such binding resulting in subsequent transcriptional activation of these genes. Importantly, these results have been validated in invasive cancer cells with different migration assays (transwells, wound closure, etc.) (cf. FIGS. 8 and 9).

These results have obvious implications for the assessment of the clinical outcome of diseases involving undesired cell migration. In particular, they demonstrate that the RelB subunit of NFκB, once phosphorylated at serine 472, contributes to the metastatic behavior of cancer cells.

Consequently, the present Inventors propose to monitor the phosphorylation status of the serine 472 of the RelB subunit of NFκB in order to i) evaluate if the RelB-dependent NFκB pathway is activated in a sample (whatever the stimulus of this activation is), ii) assess the migratory capacity of cells present in a sample, iii) prognose the clinical outcome of a disease involving undesired cell migration, and iv) design new treatments or dosage regimen or adapt previous treatments for treating said diseases.

In a first aspect, the present invention relates to an in vitro method for detecting the activation of the RelB-dependent NFκB pathway in one sample, the said method comprising the step of a) detecting the phosphorylation of serine 472 of the RelB protein of SEQ ID NO:1, or of a corresponding serine in a RelB homolog, in said sample.

In a preferred embodiment, the activation of the RelB-dependent NFκB pathway is detected if said phosphorylation is detected.

NFκB (Nuclear Factor-KappaB) is a heterodimeric protein composed of different combinations of members of the Rel family of transcription factors, including NFκB1 (p50), NFκB2 (p52), RelA (p65), RelB, and c-Rel (Rel). Hetero and homo-dimerization of NFκB proteins which exhibit differential binding specificities includes p50/RelA, p50/c-Rel, p52/c-Rel, p65/c-Rel, RelA/RelA, p50/p50, p52/p52, RelB/p50 and RelB/p52 and numerous other complexes.

NFκB is known to be important in regulating a variety of cellular responses. It belongs to the category of "rapid-acting" primary transcription factors, i.e., transcription factors that are present in cells in an inactive state and do not require new protein synthesis to be activated. This allows NFκB to be a first responder to harmful cellular stimuli. Known inducers of NFκB activity are highly variable and include reactive oxygen species (ROS), tumor necrosis factor alpha (TNFα), interleukin 1-beta (IL-1β), bacterial lipopolysaccharides (LPS), Toll-like receptors (TLRs), lymphotoxin-α, lymphotoxin-β, BAFF, RANKL, isoproterenol, cocaine, and ionizing radiation.

By "activation of the RelB-dependent NFκB pathway", it is herein meant the transmission of a cellular signal through the RelB branch of the NFκB pathway, said signal leading to a specific cellular response. As explained above, the NFκB pathway can act inter alia through the RelA or RelB transcription factors. More specifically, the activation of the RelB-dependent NFκB pathway of the invention corresponds to the transduction of a cellular signal by the NFκB pathway through the RelB subunit of the NFκB complex and not through the RelA subunit of the NFκB complex.

This activation may be due to various stimuli, such as TNF-α, interleukin 1-beta (IL-1β), bacterial lipopolysaccharides (LPS), Toll-like receptors (TLRs), lymphotoxin-α, lymphotoxin-β, BAFF, RANKL, isoproterenol, cocaine, and ionizing radiation. In particular, it may be due to TNF-α, lymphotoxin-α or lymphotoxin-β stimulation.

There is currently no reliable and easy tool for detecting and measuring the activation level of the RelB-dependent NFκB pathway.

By contrast, the present Inventors demonstrate here that RelB is phosphorylated on serine 472 by the IκB kinase in response to specific extracellular ligands (TNF-α or lymphotoxin-β) and that this specific phosphorylation allows to precisely and reliably monitor the activation of the RelB-dependent non-canonical NF-κB signaling pathway. In addition, phosphorylation of RelB by an IκB kinase complex on serine 472 residue leads to the transcription of a define set of genes (e.g., the MMP3 gene) that are involved in cell migration.

Inventors have surprisingly discovered that the expression of genes known to be activated by RelB (such as Enpp2, CXCL12, PTX3, Snail and cIAP1, see FIG. 5C) is not dependent of said S472 phosphorylation and that only pro-migratory genes are transcriptionally activated once RelB undergoes S472 phosphorylation. As a matter of fact, the results of the Inventors demonstrate that these S472-phosphorylation dependent genes belong to the Matrix Metalloproteinases family (MMP) (see examples below). Activation of RelB through Ser472 thus appears to be highly specific of a migratory behaviour.

Therefore, the specific activation of RelB identified by the Inventors may be followed by i) detecting if the RelB subunit of the NFκB complex is phosphorylated on serine 472 (or on a corresponding serine residue) and/or ii) measuring the expression level of known pro-migratory proteins such as MMPs (and in particular, MMP3).

Since protein phosphorylation is nowadays easily detected and measured by conventional means, the results of the inventors enable the detection of the activation of the RelB-dependent NFκB pathway simply and reproducibly.

The RelB protein or homolog thereof which is phosphorylated at serine 472 or at a corresponding serine residue on said RelB homolog is referred herein as the "biomarker of the invention".

RelB is one of the five members of the NFκB family, which includes RelA (p65), RelB, c-Rel (Rel), NFκB1 (p50 and its precursor p105) and NFκB2 (p52 and its precursor p100). RelB is the only NFκB member that cannot homodimerize and only triggers potent transcriptional activation when coupled to p50 or p52. In human, the RelB protein has the sequence represented by SEQ ID NO:1 (NCBI NP_006500.2), and carries on position 472 a serine residue.

As used herein, the term "RelB homolog" refers to a homolog of SEQ ID NO:1. This homolog is for example the mouse RelB protein of SEQ ID NO:2 (NP_033072.2), the rat RelB protein of SEQ ID NO:3 (XP_002728953.1), the cattle RelB protein of SEQ ID NO:4 (XP_002695213.1), etc.

More generally, a "RelB homolog" is a protein whose sequence shares at least 80% homology with the RelB protein of SEQ ID NO:1, while retaining the RelB function, e.g. the capacity of binding p50 or with DNA, that can be demonstrated for example by electrophoretic mobility shift assay (Derruder et al, JBC 2003). Preferably, the amino acid sequences of the homologs of the RelB protein are identical at more than 80%, preferably 81%, more preferably 82%, more preferably 83%, more preferably 84%, more preferably 85%, preferably 86%, more preferably 87%, more preferably 88%, more preferably 89%, more preferably 90%, more preferably 91%, more preferably 92%, more preferably 93%, more preferably 94%, more preferably 95%, more preferably 96% to the and even more preferably 97% to SEQ ID NO:1. Preferably, amino acid sequence identity is measured by using the global alignment algorithm of Needleman and Wunsch (*J. Mol. Biol.* 1970).

It is noteworthy that the amino acid sequence of RelB is highly conserved among the mammalian species (see FIG. 3). When a homolog protein is aligned with RelB using a convenient software (for example the "BLAST 2 sequences" software (Tatusova et al., «Blast 2 sequences—a new tool for comparing protein and nucleotide sequences», *FEMS Microbiol.*, 1999), it is observed that the serine residue aligning to serine 472 may correspond to a slightly different position in the said homolog amino acid sequence.

Consequently, as used herein, the terms "corresponding serine in a RelB homolog" or "corresponding serine" refer to the serine residue in a RelB homolog which corresponds to the serine 472 of SEQ ID NO:1 when said RelB homolog is aligned with SEQ ID NO:1 with a conventional software. For example serine 451 in SEQ ID NO: 2 is the corresponding serine residue in RelB homolog of the species *Mus musculus*.

As used herein, the term "sample" relates to any sample that may be used in a research laboratory or any biological sample. The sample may for example be deprived of any cells and contain only purified proteins or nucleic acids that are to be studied. The sample may also be a biological sample taken from a subject. Such a biological sample must allow for the determination of the expression levels of the biomarker of the invention. The nature of the biological sample will thus be dependent on the nature of the disorder. Preferred biological samples for the determination of the phosphorylation level of Ser472-RelB include samples such as a tissue sample, a blood sample, a urine sample, a plasma sample, or a lymph sample. Preferably, the term "sample" designates a cell extract or a protein extract.

Cell extracts can be obtained by conventional means. Historically, physical lysis was the method of choice for cell disruption and extraction of cellular contents; however, it often requires expensive, cumbersome equipment and involves protocols that can be difficult to repeat due to variability in the apparatus. Also, traditional physical disruption methods are not conducive for high throughput and smaller volumes typical of modern laboratory research. In recent years, detergent-based lysis methods have become the norm. Through empirical testing by trial and error, different detergent-based solutions composed of particular types and concentrations of detergents, buffers, salts and reducing agents have been developed to provide the best possible results for particular species and types of cells. Detergents have both lysing and solubilizing effects. When the goal of cell lysis is to purify or test the function of a particular protein, special attention must be given to the effects of the lysis reagents on the stability and function of the protein(s) of interest. Certain detergents will inactivate the function of particular enzymes, and long-term stability of extracted/purified proteins often requires that they be removed from the initial lysis reagents and/or stabilized by addition of particular compounds. The skilled person will be able to adapt the usually used protocols and reagents to the detection of the phosphorylated protein of the invention. Commercially available reagents are preferred.

According to the present invention, a serine phosphorylation is a post-translational modification in which a covalently bound phosphate group ($PO_4^{3-}$) is added onto a serine by a specific protein kinase. Such a phosphorylation results in a change of both the mass and the charge of the amino acid which is phosphorylated.

The detection of serine 472 phosphorylation can be achieved with usual immunoassay techniques, such as immunoprecipitations, Western blotting, ELISAs, other sandwich assays, FACS analysis and cross-linking assays, and any other means known to the person of skills in the art. Specific reagents can be used to detect and/or quantify the phosphorylated RelB protein, and to determine the distinct amounts of the phosphorylated and non-phosphorylated forms. For example, the phosphorylated and the non-phosphorylated forms of the RelB protein can be identified on the basis of their respective different electrophoresis mobility by Western blotting with an antibody against RelB or with antibodies recognizing specifically the Ser472-phosphorylated RelB protein. Alternatively, the total amount of phosphorylated RelB protein can be assessed by ELISA with antibodies recognizing specifically the Ser472-phosphorylated RelB protein. The skilled person will realize that it may be preferable to first isolate the RelB protein, e.g. by immunoprecipitation or affinity chromatography, before determining the amount of phosphorylated protein.

Phosphorylation can also be conveniently determined by mass spectrometry (MS) following isolation of the protein of interest, i.e. the RelB protein. MS requires less analyte material to provide high-quality information about peptides than other current methods. Accordingly, in a preferred embodiment, purified RelB protein or fragments thereof are characterized by mass spectrometry (MS), matrix-assisted laser desorption/ionization time-of-flight (MALDI-TOF) mass spectrometry, tandem mass spectrometry (MS-MS), and/or MS 3 analysis. In one preferred embodiment, matrix-assisted laser desorption/ionization time-of-flight (MALDI-TOF) mass spectrometry is utilized to measure the masses of purified peptides. MALDI-TOF mass spectrometry is useful for rapidly screening samples before analyzing them by other, more complex methods such as tandem mass spectrometry (MS/MS) (see below), and is both sensitive and simple.

In a preferred embodiment, the phosphorylation of the RelB protein on serine 472 or on the corresponding serine, is detected by means of a reagent selected from the group consisting of: an antibody, an aptamer, an intrabody and an AQUA peptide.

This reagent, which is intended to detect specifically if the serine 472 of the RelB protein of SEQ ID NO:1 (or the corresponding serine in a RelB homolog) is phosphorylated, is also encompassed in the present invention. Said reagent is specific of the RelB protein phosphorylated on serine 472 and as such will not detect other phosphorylated serine (such as PSR-45b antibody). In the context of the invention, said reagent will be referred to hereafter as "the reagent of the invention".

In a preferred embodiment, the reagent of the invention is an isolated phosphorylation site-specific antibody that specifically binds the RelB protein of SEQ ID NO:1 or an homolog thereof only when said protein or homolog is phosphorylated on serine 472 or on a corresponding serine. Preferably, said antibody does not bind said RelB protein or homolog when it is not phosphorylated on said serine. Said antibody is hereafter referred to as "the antibody of the invention".

The terms "antibody", "antibodies" or "immunoglobulin" are used interchangeably throughout this application. They should be construed in the broadest sense: these terms, as used herein, thus include monoclonal antibodies (e.g., full length or intact monoclonal antibodies), polyclonal antibodies, multivalent antibodies or multispecific antibodies (e.g., bispecific antibodies so long as they exhibit the desired biological activity) and functional fragments thereof.

The term "antibody" as used herein designates a polypeptide that exhibit binding specificity to a specific antigen. More particularly, an antibody (or "immunoglobulin") consists of a glycoprotein comprising at least two heavy (H) chains and two light (L) chains inter-connected by disulfide bonds.

Each heavy chain comprises a heavy chain variable region (or domain) (abbreviated herein as $V_H$) and a heavy chain constant region (hereafter $C_H$). Heavy chains are classified as gamma, mu, alpha, delta, or epsilon, and define the antibody's isotype as IgG, IgM, IgA, IgD, and IgE, respectively. The $C_H$ region of the immunoglobulin IgG, IgD, and IgA (γ, δ and α chains respectively) comprises three domains (CH1, CH2, and CH3) and a hinge region for added flexibility, while the $C_H$ region of the immunoglobulin IgM and IgE contains 4 domains (CH1, CH2, CH3, and CH4).

IgG antibodies are classified in four distinct subtypes, named IgG1, IgG2, IgG3 and IgG4. The structure of the hinge regions in the γ chain gives each of these subtypes its unique biological profile (even though there is about 95% similarity between their Fc regions, the structure of the hinge regions is relatively different).

Each light chain comprises a light chain variable region (abbreviated herein as $V_L$) and a light chain constant region comprising only one domain, $C_L$. There are two types of light chain in mammals: the kappa (κ) chain, encoded by the immunoglobulin kappa locus on chromosome 2, and the lambda (λ) chain, encoded by the immunoglobulin lambda locus on chromosome 22.

The $V_H$ and $V_L$ regions can be further subdivided into regions of hypervariability, termed "Complementarity Determining Regions" (CDR), which are primarily responsible for binding an antigen, and which are interspersed with regions that are more conserved, designated "Framework Regions" (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The assignment of amino acid sequences to each domain is in accordance with well-known conventions (for example, the IMGT unique numbering convention as disclosed by Lefranc, M.-P., et al., Dev. Comp. Immunol., 27, 55-77 (2003)). The functional ability of the antibody to bind a particular antigen depends on the variable regions of each light/heavy chain pair, and is largely determined by the CDRs. The variable region of the heavy chain differs in antibodies produced by different B cells, but is the same for all antibodies produced by a single B cell or B cell clone (or hybridome). By contrast, the constant regions of the antibodies mediate the binding of the immunoglobulin to host tissues or factors, including various cells of the immune system (e.g. effector cells) and the first component (C1q) of the classical complement system.

An "epitope" is the site on the antigen to which an antibody binds. It can be formed by contiguous residues or by non-contiguous residues brought into close proximity by the folding of an antigenic protein. An epitope in particular can comprise a residue carrying a specific post-translational modification, e.g. a glycosylation or a phosphorylation, said specific post-translational modification ensuring specific reconnaissance by the antibody. For example, in the present case, the epitope which is recognized by the antibody of the invention is a group of contiguous residues or by non-contiguous residues brought into close proximity by the folding of an antigenic protein, said residues comprising the phosphorylated serine 472 residue or a corresponding serine residue. By contrast, the same group of residues comprising the unphosphorylated serine 472 is not recognized by the antibody of the invention.

As used herein, the term "antibody fragments" intends to designate Fab, Fab', F(ab')2, scFv, dsFv, ds-scFv, dimers, minibodies, diabodies, and multimers thereof and bispecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

A "functional fragment" of an antibody means in particular an antibody fragment as defined above, with the same binding activity to phosphorylated RelB as the parental antibody.

In the context of the present invention, an antibody is said to "recognize" or "bind" a peptide having a define sequence if said antibody has an affinity constant $K_a$ (which is the inverted dissociation constant, i.e. $1/K_d$) higher than $10^6$ $M^{-1}$, preferably higher than $10^7$ $M^{-1}$, more preferably higher than $10^8$ $M^{-1}$ for said peptide. Also, in the context of the present invention, an antibody is said to "specifically bind" or to "specifically recognize" a peptide if said antibody has an affinity constant $K_a$ greater than $10^7$ $M^{-1}$, preferably greater than $10^8$ $M^{-1}$, more preferably greater than $10^9$ $M^{-1}$ for said peptide and even more preferably greater than $10^{10}$ $M^{-1}$ for said peptide and has an affinity constant $K_a$ lower than $10^5$ $M^{-1}$ for all the other peptide.

The affinity constant which is used to characterize the binding of antibodies (Ab) to a peptide or an antigen (Ag) is the inverted dissociation constant defined as follows:

$$Ab + Ag \leftrightarrows AbAg$$

$$K_a = \frac{[AbAg]}{[Ab][Ag]} = \frac{1}{K_d}$$

This affinity can be measured for example by equilibrium dialysis or by fluorescence quenching, both technologies being routinely used in the art.

In a preferred embodiment, the antibodies of the invention bind the Ser472 phosphorylated RelB protein with a $K_D$ of less than $10^{-7}$ M, preferably from less than $10^{-5}$ M. In a further preferred embodiment, the antibodies of the invention bind the Ser472 phosphorylated RelB protein with a $K_D$ of less than $10^{-9}$ M, preferably from less than $10^{-10}$ M.

More preferably, the antibodies of the invention do not bind the RelB protein when said protein is not phosphorylated on Ser 472 (or on a corresponding serine residue). In particular, the antibodies of the invention have an affinity constant $K_a$ which is less than $10^5$ $M^{-1}$ for the RelB protein which is not phosphorylated on Ser472. More particularly, the antibodies of the invention have an affinity constant $K_a$ which is less than $10^5$ $M^{-1}$ for all polypeptides, except with the Ser472-phosphorylated RelB protein.

The antibody of the invention may be monoclonal or polyclonal and may be of any species of origin, including (for example) mouse, rat, rabbit, horse, or human, or may be chimeric antibodies.

A "polyclonal antibody" as used herein, refers to an antibody that is obtained from different B cells. It typically includes various antibodies directed against various determinants, or epitopes, of the target antigen. Polyclonal phosphorylation site specific antibodies that specifically bind RelB only when phosphorylated at the serine 472 or a corresponding serine residue may be produced by standard antibody production methods, for example by i) immunizing a suitable animal (e.g., rabbit, goat, etc.) with the phosphorylated protein of the invention or with an immunogenic peptide, ii) collecting immune serum from the animal, and iii) separating the polyclonal antibodies from the immune serum, in accordance with known procedures.

Immunogenic peptides suitable for producing antibodies of the invention may be designed, constructed and employed according to techniques used in the art (see e.g. Czernik, *Methods In Enzymology*, 1991; Merrifield, *J. Am. Chem. Soc.* 1962). Preferably, an immunogenic peptide comprises only a portion of the protein of SEQ ID NO. 1 immediately flanking the phosphorylatable serine, i.e. the immunogenic peptide is a peptide of a specific length, said peptide comprising a group of residues which necessarily includes serine 472.

In one particular aspect, the present invention also relates to an isolated immunogenic peptide containing at least 5 consecutive amino acid residues of the RelB protein of SEQ ID NO:1 or of an homolog thereof, said immunogenic peptide containing the phosphorylated serine residue located in position 472 of SEQ ID NO:1 or a corresponding serine residue on said RelB homolog.

Preferably, said immunogenic peptide contains at least 8, more preferably at least 10, and even more preferably at least 12 consecutive amino acid residues of the RelB protein of SEQ ID NO:1 or of an homolog thereof, and contains the phosphorylated serine residue located in position 472 of SEQ ID NO:1 or a corresponding serine residue on said RelB homolog. Preferably, said immunogenic peptide contains no more than 25, more preferably no more than 20, and even more preferably no more than 15 consecutive amino acid residues of the RelB protein of SEQ ID NO:1 or of an homolog thereof.

Preferred immunogenic peptides are peptides consisting essentially of about 10 to 15 amino acids of SEQ ID NO:1 including the phosphorylated serine 472 or a corresponding serine in a RelB homolog, wherein about 3 to 8 amino acids are positioned on each side of said phosphorylated serine.

For example, the immunogenic peptide of SEQ ID NO:5 may be used to produce the antibodies of the invention. It will be appreciated by those of skill in the art that longer or shorter immunogenic peptides may also be employed.

In a preferred embodiment, the immunogenic peptide of the invention has the sequence GTVSLPGLEPPGG (SEQ ID NO:5), the Serine in position 4 of said SEQ ID NO:5 being phosphorylated ($PO_3H_2$).

This immunogenic peptide can be synthetized by conventional means and can be used to generate the polyclonal antibody of the invention. Convenient polyclonal antibodies have been accordingly obtained and successfully used by the Inventors (see the experiments below).

In a preferred embodiment, the said phosphorylation site-specific antibody is a monoclonal antibody.

A "monoclonal antibody", as used herein, means an antibody arising from a nearly homogeneous antibody population. The individual antibodies of a population are identical except for a few possible naturally-occurring mutations which can be found in minimal proportions. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is characterized by heavy chains of one and only one isotype and subtype, and light chains of only one type. Monoclonal antibodies are highly specific and are directed against a single epitope of an antigen. Monoclonal antibodies may be produced by a single clone of B cells or "hybridoma". Monoclonal antibodies may also be recombinant, i.e. produced by protein engineering. The invention relates to monoclonal antibodies isolated or obtained by purification from natural sources or obtained by genetic recombination or chemical synthesis.

The monoclonal antibodies of the invention may be produced in a hybridoma cell line according to the well-known technique of Kohler and Milstein, Nature 1975; Kohler and Milstein, Eur. J. Immunol. (1976); see also, CURRENT PROTOCOLS IN MOLECULAR BIOLOGY, Ausubel et al. (1989). Monoclonal antibodies so produced are highly specific, and improve the selectivity and specificity of diagnostic assay methods provided by the invention.

For example, a solution containing the appropriate antigen may be injected into a mouse or other species and, after a sufficient time (in keeping with conventional techniques), the animal is sacrificed and spleen cells obtained. The spleen cells are then immortalized by fusing them with myeloma cells, typically in the presence of polyethylene glycol, to produce hybridoma cells. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

The invention also provides immortalized cell lines that produce the monoclonal antibody of the invention. For example, hybridoma clones, constructed as described above, that produce monoclonal antibodies binding specifically the RelB-phosphorylated form disclosed herein are provided. In a preferred embodiment, said immortalized cell lines are llama hybridoma, a rabbit hydridoma or mouse hybridoma.

Monoclonal Fab fragments may also be produced in *Escherichia coli* by recombinant techniques known to those skilled in the art (W. Huse, Science 246: 1275-81 (1989); Mullinax et al., PNAS 1990). If monoclonal antibodies of one isotype are preferred for a particular application, particular isotypes can be prepared directly, by selecting from the initial fusion, or prepared secondarily, from a parental hybridoma secreting a monoclonal antibody of different isotype (Steplewski, et al., PNAS 1985; Spira et al., J. Immunol. Methods, 1984). The invention includes recombinant cells producing an antibody of the invention, which cells may be constructed by well-known techniques; for example the antigen combining site of the monoclonal antibody can be cloned by PCR and single-chain antibodies produced as phage-displayed recombinant antibodies or soluble antibodies in *E. coli*.

Antibodies of the invention specifically bind the RelB protein when phosphorylated on serine 472 (or a corresponding serine in a RelB homolog), and do not bind to the non-phosphorylated form. This specificity may be screened according to standard techniques (Czernik et al., Methods in Enzymology, 201: 264-283 (1991)) such as ELISA. Also, peptide competition assays may be carried out to confirm lack of reactivity with other epitopes on the RelB protein. The antibodies of the invention may also be tested by Western blotting against cell preparations containing RelB proteins mutated the on the serine 472 residue, so as either to not accept phosphorylation (e.g. serine to alanine mutants, see examples in the experimental examples section herebelow) or to mimic constitutive phosphorylation on this residue (e.g. serine to aspartate or glutamate mutants). Such mutations are well known in the art. Antibodies may be further characterized via immunohistochemical (IHC) staining using normal and pathologic tissues to examine RelB-S472 phosphorylation and activation status of the NFkB pathway in said tissues. IHC may be carried out on paraffin-embedded tissues according to well-known techniques, for example comprising the steps of: i) deparaffinizing tissue sections with xylene followed by ethanol; ii) hydrating in water then PBS; iii) unmasking antigen by heating slide in sodium citrate buffer; iv) incubating sections in hydrogen peroxide; v) blocking in blocking solution; vi) incubating slide in primary antibody and secondary antibody; and finally vii) detecting using ABC avidin/biotin method according to manufacturer's instructions (see ANTIBODIES: A LABORATORY MANUAL, Chapter 10, Harlow & Lane Eds., Cold Spring Harbor Laboratory (1988)). The antibodies of the invention may be further characterized by flow cytometry carried out according to standard methods (Chow et al., Cytometry (Communications in Clinical Cytometry) 2001).

Antibodies of the invention may also be advantageously conjugated to fluorescent dyes (e.g. Alexa-488, PE) for use in multiparametric analyses along with other signal transduction and/or cell marker antibodies.

The phosphorylation-site specific antibodies of the invention specifically bind homolog RelB proteins that are phosphorylated at the serine 472 site or a corresponding serine thereof. In other words, the invention includes antibodies that bind the conserved phosphorylatable serine in respective RelB proteins from other species (e.g. mouse, rat, monkey, yeast).

Two different monoclonal antibodies have been generated by the inventors against the RelB protein of SEQ ID NO:1 which is phosphorylated on serine 472 (see examples below). These antibodies can be used for example to highlight the presence of S472-phosphorylated RelB by immunohistochemistry (FIG. 11A, see also FIGS. 1D, 1E and 11B). They are therefore advantageously used in order to carry out the methods of the invention.

In a preferred embodiment, the reagent of the invention is an aptamer which binds, in a phospho-specific manner, essentially the same phosphorylatable epitope to which the phosphospecific antibody of the invention binds (Neuberger et al., Nature 1984). Said aptamer is preferably a nucleic acid-based aptamer. Nucleic acid-based aptamers are being developed for a variety of diagnostic applications, including detection of a wide range of non-nucleic acid analytes (Conrad et al, *Methods Enzymol*, 1996). Aptamers can be selected in vitro by the SELEX process from very large populations of random sequence oligomers (Ellington et Szostak, *Nature* 1990). This well-established methodology selects aptamers based on their affinity for a specific target molecule. Aptamers can be selected against nearly any class of molecule including proteins, ranging from simple peptides to post-translationally modified proteins. The post-translational modifications potentially detectable by aptamers include a variety of common covalent modifications such as phosphorylation, glycosylation, and proteolytic cleavage and noncovalent modifications such as conformational changes due to binding of ligands (McCauley et al, *Analytical Biochemistry* 2003).

In a preferred embodiment, the reagent of the invention is an intrabody which binds, in a phospho-specific manner, essentially the same phosphorylated epitope to which the phosphospecific antibody of the invention binds. An intrabody is an antibody that works within the cell to bind to an intracellular protein. Due to the lack of a reliable mechanism for bringing antibodies into the cell from the extracellular environment, this typically requires the expression of the antibody within the target cell, which can be accomplished by gene therapy (Rinaldi A S et al, *Exp. Cell. Res.* 2013; Chen et al, *Human Gene Therapy* 1994). As a result, intrabodies are defined as antibodies that have been modified for intracellular localization. The antibody may remain in the cytoplasm, or it may have a nuclear localization signal. Because antibodies ordinarily are designed to be secreted from the cell, intrabodies require special alterations, including the use of single-chain antibodies (scFvs), and modification of immunoglobulin VL domains for hyperstability. Such optimizations have improved the stability and structure of intrabodies, allowing the publication of a variety of promising applications (Mhashilkar A M et al, *The EMBO Journal*, 1995).

The phosphorylated RelB protein identified by the present Inventors also enables the production of corresponding heavy-isotope labeled peptides ("AQUA peptides") for the absolute quantification of the phosphorylated or non-phosphorylated RelB protein in biological samples. Such peptides are widely used and are well known in the art (see for example WO 03/016861, and Gerber et al. *PNAS* 2003).

Briefly, an AQUA Peptide is a synthetic peptide corresponding to a peptide of interest (here a fragment of the RelB protein comprising the serine of interest). Each AQUA peptide incorporates one stable isotope labeled amino acid, creating a slight increase (6-10 daltons) in molecular weight. When mixed, the native peptide and the synthetic AQUA Peptide elute together chromatographically, migrate together electrophoreticly, and ionize with the same intensity. However, by mass spectrometry, the native peptide and the synthetic AQUA Peptide are easily distinguished. In a typical AQUA experiment, a known amount of an AQUA Peptide is added to a biological protein sample. The sample is then digested and analyzed by HPLC-MS. Extracted ion chromatograms are generated for the native peptide and the synthetic AQUA Peptide internal standard. Using peak ratios, the quantity of native peptide is calculated. Protein-AQUA is a powerful and enabling technology. For proteomics researchers, it facilitates focused, quantitative studies of not only specific protein expression, but specific amino acid modification as well. AQUA peptides are commercially available for example through the SIGMA Aldrich supplier.

Thus, in a preferred embodiment, the reagent of the invention is an AQUA peptide.

This AQUA peptide will preferably have a size that minimizes the chances that the peptide sequence will be repeated elsewhere in other non-target proteins, i.e., of at least about 6 amino acids. Also, its size will be optimized to maximize ionization frequency, i.e., it should not be longer than about 20 amino acids. The sequence of said AQUA peptide is thus preferably ranged from about 7 to about 15 amino acids. This sequence is also selected so that it is not likely to be chemically reactive during mass spectrometry. Consequently, sequences comprising cysteine, tryptophan, or methionine should be avoided. Moreover, the said AQUA peptide contains one or more labeled amino acids (i.e. the label is an actual part of the peptide) or, less preferably, labels may be attached after synthesis according to standard methods. Preferably, the label is a mass altering label selected based on the following considerations: the mass should be unique to shift fragments masses produced by MS analysis to regions of the spectrum with low background; the ion mass signature component is the portion of the labeling moiety that preferably exhibits a unique ion mass signature in MS analysis; the sum of the masses of the constituent atoms of the label is preferably uniquely different than the fragments of all the possible amino acids. Finally, the label should be robust under the fragmentation conditions of MS and not undergo unfavorable fragmentation. Labeling chemistry should be efficient under a range of conditions, particularly denaturing conditions, and the labeled tag preferably remains soluble in the MS buffer system of choice. The label may contain a mixture of two or more isotopically distinct species to generate a unique mass spectrometric pattern at each labeled fragment position. Stable isotopes, such as 2H, $^{13}$C, $^{15}$N, $^{17}$O, $^{18}$O, or $^{34}$S, are among preferred labels. The production and use of AQUA peptides for the absolute quantification of proteins in complex mixtures has been described in WO 03/016861, and in Gerber et al. *PNAS* 100: 6940-5 (2003)).

Preferably, the AQUA peptide of the invention comprises at least 8 consecutive amino acids from SEQ ID NO:1 or from an homolog thereof, and comprises the serine 472 or corresponding serine residue in said RelB homolog.

The reagent of the invention, and in particular the aptamers, the intrabodies, the antibodies and/or the AQUA peptides of the invention, may also be included within a kit, said kit being hereafter referred to as the "kit of the invention". This kit may comprise at least one phosphorylation site-specific antibody, one aptamer, or one AQUA peptide as defined previously. When the kit of the invention contains the antibody of the invention, a secondary antibody conjugated to a detectable label is preferably included.

The kit of the invention may also include ancillary agents such as buffering agents and protein stabilizing agents, e.g., polysaccharides and the like. This kit may further include, where necessary, agents for reducing background interference in a test, control reagents, apparatus for conducting a test, and the like. The kit of the invention may be packaged in any suitable manner, typically with all elements in a single container along with a sheet of printed instructions for carrying out the methods of the invention.

This kit is preferably used in order to carry out the detecting method of the invention, which is thoroughly described above. It may also be used to carry out the methods disclosed below.

In a particular embodiment, this kit contains the monoclonal antibodies that have been generated by the inventors in order to detect specifically the phosphorylation level of serine 472 of the RelB protein.

In a preferred embodiment, the detecting method of the invention further comprises the step of b) measuring the phosphorylation level of serine 472 of the RelB protein of SEQ ID NO:1, or of a corresponding serine in a RelB homolog, in said sample.

Measuring the phosphorylation level of a phosphorylated residue can be achieved by any conventional techniques known in the art. For example, one can use classical immunoassays such as radioimmunoassay, immunofluorescence assays, enzyme-linked immunoassays, and the like. Preferred techniques are mass spectrometry-based assays such as those described above, as these assays enable to quantify precisely the amount of the target phosphorylated polypeptide (Mann et al, *Trends in Biotechnology;* 2002). These conventional techniques may use the antibodies of the invention.

In a more preferred embodiment, the detecting method of the invention further comprises the steps of:

c) comparing the phosphorylation level obtained in step b) with a reference phosphorylation level, and d) determining the activation of the RelB-dependent NFκB pathway in said sample.

In this embodiment, the activation of the RelB-dependent NFκB pathway is preferably detected if said phosphorylation level obtained in b) is superior to said reference phosphorylation level.

As used herein, the term "reference phosphorylation level" designates a predetermined phosphorylation level obtained from a sample with a known level of Ser472-phosphorylated RelB protein. This latter sample is called hereafter a "reference sample". In particular embodiments, the said reference sample may be a sample containing purified Ser472 non-phosphorylated RelB protein, or a biological sample containing essentially cells in which the RelB-dependent NFκB pathway is not activated.

Activation of the RelB-dependent NFκB pathway can be performed by (i) extracellular effectors for example specific cytokines of the TNFα family (LTβ, CD40L, BAFF, TWEAK), (ii) stabilization of the NIK kinase, (iii) by expressing mutant forms of p100, the main RelB inhibitor, thereby preventing its association with RelB or leading to its constitutive degradation, and (iv) by overexpressing RelB.

Vice a versa, blockage in RelB-dependent NFκB pathway can be performed by (i) expressing dominant negative mutant forms of p100 whose proteolysis cannot be induced upon extracellular stimulation, (ii) by using antagonist antibody against specific receptors whoses ligands are known inducers of the RelB-dependent NFκB pathway, (iii) by inducing constitutive degradation of NIK, and (iv) by expressing mutant form of RelB that has an alanine instead of a serine in position 472.

Preferably, the reference sample contains essentially cells in which the RelB-dependent NFκB pathway has not been activated. More preferably, the reference sample contains purified Ser472 non-phosphorylated RelB protein.

As mentioned previously, the detecting method of the invention may require the comparison of the phosphorylation level on serine 472 of the RelB protein in the tested sample with a reference phosphorylation level, in order to conclude, if said phosphorylation level is superior to said reference value, that the RelB-dependent NFκB pathway is activated in said sample.

In the context of the invention, it is meant that the phosphorylation level which is measured in the tested sample is "superior to a reference value" if it is 2 fold superior, preferably 4 fold, and more preferably 6 fold superior to said reference value. In other word, it is meant that the phosphorylation level which is measured in the tested sample is "superior to a reference value" for example if the ratio between said phosphorylation level and said reference value is of at least 2, of at least 4 or of at least 6.

On the contrary, it is meant that the phosphorylation level which is measured in the tested sample is "similar to a reference value" for example if the ratio between said phosphorylation level and said reference value is comprised between 0.8 and 1.2, preferably between 0.9 and 1.1, more preferably between 0.95 and 1.05.

The person skilled in the art will understand that the phosphorylation level of the RelB protein in the test and in the reference samples should be normalized to the total amount of the RelB protein in said samples, or to the amount of a reference protein, e.g. beta-tubulin, in said samples, Such a normalization facilitates the comparison of the levels of phosphorylation between the tested sample and the reference sample.

The present Inventors have demonstrated that the RelB subunit of NFκB, once phosphorylated at serine 472, binds to the endogenous promoter of migration-associated genes, said binding resulting in subsequent transcriptional activation of these genes. This binding occurs in particular in breast cancer cells. These genes belong for example to the MMP family. One of these genes is the MMP3 gene (see FIGS. 5, 6, 7 and 8A, and examples below). These results suggest that the detection of the biomarker of the invention in cells of interest (e.g., cancer cells) reveals an enhanced expression of the said RelB-dependent pro-migratory genes and, therefore, highlights the enhanced migratory capacity of these cells. The present inventors therefore propose to use the biomarker of the invention to assess the migratory behavior of cells present in a biological sample.

They moreover propose to monitor the expression level of MMPs and in particular of MMP3 to evaluate the activation level of the RelB-dependent NFκB pathway.

In another aspect, the present invention relates to an in vitro method for detecting the activation of the RelB-dependent NFκB pathway in one sample, the said method comprising the step of detecting the expression of a Matrix Metalloproteinase protein, for example the MMP9, MMP10, MMP12 or the MMP3 protein, in said sample.

Matrix metallopeptidase 3, alias "Matrix metalloproteinase 3" or "MMP3" is also known as Stromelysin-1. This enzyme is encoded in humans by the MMP3 gene. Human MMP3 has for example the SEQ ID NO:6 (NP_002413). The MMP3 gene is part of a cluster of MMP genes which localizes to chromosome 11q22.3. MMP-3 has an estimated molecular weight of 54 kDa. The MMP-3 enzyme degrades collagen types II, III, IV, IX, and X, proteoglycans, fibronectin, laminin, and elastin. In addition, MMP-3 can also activate other MMPs such as MMP-1, MMP-7, and MMP-9, rendering MMP-3 crucial in connective tissue remodeling. The enzyme is thought to be involved in wound repair, progression of atherosclerosis, and tumor initiation.

Matrix metallopeptidase 9 alias "Matrix metalloproteinase 9" or MMP-9", is also known as 92 kDa type IV collagenase, 92 kDa gelatinase or gelatinase B (GELB). This enzyme is encoded in humans by the MMP9 gene. Human MMP9 has for example the SEQ ID NO:7 (NP_004985). The MMP9 enzyme degrades type IV and V collagens. MMP9 is involved in the development of several human malignancies, as degradation of collagen IV in basement membrane and extracellular matrix facilitates tumor progression, including invasion, metastasis, growth and angiogenesis.

Matrix metalloproteinase-10 or "MMP10" is also called Stromelysin-2 or transin-2. This enzyme is encoded in humans by the MMP10 gene which localizes on chromosome 11q22.3.

Human MMP10 has for example the SEQ ID NO:8 (NP_002416). The MMP10 enzyme degrades proteoglycans and fibronectin. It has been linked to cancer stem cell vitality and metastasis (Justilien V., *PloS ONE* 2012).

Matrix metalloproteinase-12 or "MMP12" is also called macrophage metalloelastase (MME) or macrophage elastase (ME). This enzyme is encoded in humans by the MMP12 gene which localizes on chromosome 11q22.3. Human MMP12 has for example the SEQ ID NO:9 (NP_002417.2). The MMP12 enzyme degrades soluble and insoluble elastin. MMP12 may play a role in aneurysm formation and studies in mice and humans suggest a role in the development of emphysema (Curci et al, *J. Clin. Invest* 1998; Woodruff P G et al, *Am. J. Resp. Crit. Care Med.* 2005).

The expression of Matrix Metalloproteinase proteins can be assessed by any conventional means, for example by detecting the mRNA of said protein or by detecting the protein level by ELISA, western Blotting, or any other usual immunoassay.

In a further aspect, the present invention relates to a method for assessing the migratory behavior of cells present in a biological sample, the said method comprising the steps of:

a) detecting the activation (or not) of the RelB-dependent NFκB pathway in the cells present in said sample according to the detecting methods of the invention, and
b) determining that said cells have a migratory behavior if the RelB-dependent NFκB pathway in said cells is activated.

In this embodiment of the invention, the tested sample is preferably a biological sample containing cells of interest. This biological sample can be either a primary cell culture, or a cell line culture, or a sample obtained from a subject, said sample containing cells. The tested sample may also contain cell extracts or cell lysates.

As used herein, cells having a "migratory behavior" are meant to efficiently move and/or translate from one place to another. They are therefore not static. On the contrary, static cells do not have any migratory behavior.

In some cells, migratory ability can be constitutive, whereas in other cells, it is induced by specific external signals, including chemical signals and mechanical signals. The method of the invention is preferably used so as to detect the migratory behavior of cells whose migratory capacity is inducible. As a matter of fact, the method of the invention will enable to indirectly detect if said cells have been contacted with said specific external signals and if their migration has therefore been induced.

Until recently, the cell migratory behavior was analyzed generally either by determining the level of known pro-migratory genes or proteins expressed (cytoskeleton proteins for example), or by analyzing their migration under a microscope (wound healing assays, transwells assays, etc.).

As many genes and proteins are involved in cell migration, the first option was time-consuming and required the analysis of a number of different markers before a reliable conclusion is obtained. The method of the invention is therefore advantageous as it focuses on a single biomarker (the biomarker of the invention) so as to highlight the migratory behavior of cells. The method of the invention is also more reliable than the microscopic study of the cells, because, in the former, the cells can be maintained in their natural environment (potentially containing the external signal from which the migratory capacity results) until the cells are fixed and studied. Also, no bias is introduced by suspending them in artificial medium to permit their visualization.

The detection of the activation of the RelB-dependent NFκB pathway in the cells through the detecting method of the invention can be performed with a variety of standard assays as disclosed above. One can for example use Western Blotting, ELISA, immunohistochemical staining, flow cytometry, mass spectrometry, etc. Preferably, these assays will be conducted by using the reagent of the invention. The person skilled in the art will easily adapt and optimize the usual conditions of these assays to take into account the specific conditions to use these reagents.

In the context of the present invention, cells of interest are meant to have a migratory behavior if the RelB-dependent NFκB pathway in said cells is activated, i.e, if the phosphorylation level of the serine 472 of the RelB subunit of NFκB or of a corresponding serine thereof is superior to the reference phosphorylation level. Preferably, in this case, said reference phosphorylation level has been obtained on a reference sample containing only cells in which the RelB-dependent NFκB pathway is not activated or on a reference sample containing only purified Ser472 non-phosphorylated RelB protein. More preferably, said reference phosphorylation level has been obtained on a reference sample containing only the same cells as those that are studied, in which the RelB-dependent NFκB pathway is not activated.

Once they are induced to migrate from the initial site of tumor growth, cancer cells acquire an invasive phenotype characterized by both the loss of cell-cell interactions and increased cell motility. These cells are able to enter the blood or lymph vessels (intravasation) and cross the vessel wall to exit the vasculature (extravasation) in distal organs where they can continue to proliferate, thereby forming a second tumor mass. Cancer cell migration is typically regulated by integrins, matrix-degrading enzymes, and cell-cell adhesion molecules.

The present Inventors have shown that the expression of some of these molecules (e.g. MMP3, MMP9, MMP10, MMP12) is regulated by the RelB-dependent NFκB pathway, and, in particular, by the Ser472-phosphorylated form of RelB. They therefore propose to use the biomarker of the invention in order to assess the invasiveness of a cancer and to identify the risk that metastases appear in a subject.

Thus, in a further aspect, the present invention relates to method for identifying a cancer at risk of metastases in a subject, the said method comprising the steps of:

a) detecting the activation of the RelB-dependent NFκB pathway in the cancer cells present in a biological sample of said subject, according to the detecting methods of the invention, and
b) concluding that said subject suffers from a cancer at risk of metastases if the RelB-dependent NFκB pathway in said cancer cells is activated.

As used herein, the term "subject" includes any multicellular animal. Preferably, said subject is a mammal. Mammalian subjects include humans, non-human primates, murines, ovines, bovines, ruminants, porcines, caprines, equines, canines, felines, ayes, etc. Preferably, said subject is selected from the group consisting of: mouse, chicken, rat, human, rabbit, guinea pig, and hamster. More preferably, said subject is a human being.

In a particular embodiment, the said subject has been already diagnosed to be suffering from a cancer. In another particular embodiment, said subject is treated for said cancer.

"Metastases" refer to cancer cells that are translocated from a primary cancer site (i.e., a location where the cancer cell initially formed from a normal, hyperplastic or dysplastic cell) to a site other than the primary site, where the translocated cancer cells lodge and proliferate. By "cancer at risk of metastases" is herein meant a cancer whose cells have high migratory behavior and are able to translocate efficiently in secondary site(s). Therefore, in said subject, the risk of developing metastases is for example increased by 100%, more preferably by 200%, as compared with cancer subjects whose cancer cells have an inactived RelB-dependent NFκB pathway.

Said cancer is for example selected from the group consisting of: carcinomas such as lung cancer, breast cancer, prostate cancer, cervical cancer, pancreatic cancer, colon cancer, ovarian cancer; stomach cancer, esophagus cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, lymphoma, and leukemia.

The method of the invention is preferably applied to a subject suffering from a cancer selected from the group consisting of: prostate cancer, osteosarcoma, lung cancer, breast cancer, endometrial cancer, leukemia, glioblastoma, lymphoma, multiple myeloma, ovarian cancer, pancreatic cancer and colon cancer. The method of the invention is more preferably applied to a subject suffering from a prostate cancer, a glioblastoma or a breast cancer.

In this aspect, the term "biological sample" corresponds to a sample containing cancer cells obtained from the subject to be tested. Such as sample is hereafter designated as a "cancer sample". This sample allows the skilled person to measure the level of the biomarker of the invention in said cancer cells. In some cases, the method of the invention may further comprise a preliminary step of extracting the said cancer cells from the patient.

The cancer sample can be a tumor tissue sample or a liquid sample. When the cancer is a solid cancer, the cancer sample is preferably a tissue sample. The tissue which is the site of the tumor may still comprise non tumor healthy tissue. The "cancer sample" should thus be limited to tumor tissue taken from the patient. Said "cancer sample" may be a biopsy sample or a sample taken from a surgical resection therapy. When the cancer is a leukemia or a lymphoma, the cancer sample is preferably a liquid sample, preferably a blood sample or a lymph sample.

In this particular aspect, the "reference sample" which is used to measure the "reference phosphorylation level" in the detecting method of the invention is preferably a sample containing only normal cells in which the RelB-dependent NFκB pathway is not activated or on a reference sample containing only purified Ser472 non-phosphorylated RelB protein. More preferably, said reference sample contains only normal cells extracted from the subject to be tested, in which the RelB-dependent NFκB pathway is not activated.

As disclosed above, the detection of the activation of the RelB-dependent NFκB pathway in the cells through the detecting method of the invention can be performed with a variety of standard assays as disclosed above.

As disclosed above, production of abnormal migratory signals may induce the migration of the wrong cell type to the wrong place, which may have catastrophic effects on tissue homeostasis and overall health. Apart from metastases development, other examples include autoimmune syndromes in which immune cells home to certain locations (joints in rheumatoid arthritis, and the CNS in multiple sclerosis are two examples) and destroy the supporting tissue, causing severe damage. There are other types of alteration that cause abnormal migrations. For example, chronic inflammatory syndromes, such as asthma, rheumatoid arthritis, multiple sclerosis, psoriasis and Crohn's disease share a migratory component, i.e. the constant infiltration of immune cells into inappropriate places. Once these cells localize to their abnormal target tissues, they become activated and can cause massive damage and progressive deterioration of the tissue. Some therapies against multiple sclerosis and psoriasis are based on preventing immune cells from reaching their target tissues by counteracting receptors implicated in the abnormal homing to the CNS and skin, respectively. Finally, the migration and proliferation of vascular smooth muscle cells is also a key event in progressive vessel thickening leading to atherosclerosis and other vascular diseases. Vascular injury leads to endothelial dysfunction, which, in turn, promotes the expression of inflammatory markers and transendothelial leukocyte migration. Recruitment of leukocytes from the circulation into the vessel intima is a crucial step for the development of fibrous plaques. Cytokines are among the molecules known to upregulate endothelial cell adhesion molecules, recruit leukocytes and induce smooth muscle cell migration and proliferation.

It results from the above that all these disorders can be designated as "involving cell migration" in its broadest sense. As cell migration capacity can be efficiently determining by means of the detecting method of the invention, the present Inventors propose to use the biomarker of the invention so as to monitor the evolution of these disorders.

In a further aspect, the present invention relates to an in vitro method for monitoring the evolution of a disorder involving cell migration in a subject, the said method comprising the steps of:

a) providing at least two biological samples from the said subject, called first and second samples, the second sample having been collected from said subject after the first sample, b) detecting the activation of the RelB-dependent NFκB pathway according to the detecting methods of the invention in said at least two samples, c) comparing the phosphorylation levels measured in step b) for said first and said second samples, wherein the disorders worsens if the phosphorylation level measured in said second sample is superior to the phosphorylation level measured in said first sample.

This method will be referred to hereafter as the "monitoring method of the invention".

In this aspect, the said biological sample can be either a "solid sample" containing for example an inflammatory tissue sample or a cancer sample, or a "liquid sample", for example a blood, a plasma, a lymph, or a urine sample. In all cases, the said sample has to contain the cells of interest whose migration is likely to be involved in said disorder. Preferably, in case of an inflammatory disease, the said biological sample is a blood sample. Indeed, such a blood sample may contain the cells of interest and it may be obtained by a completely harmless blood collection from the subject. In some cases, the method of the invention may further comprise a preliminary step of extracting the said sample from the subject.

The two samples have to be obtained from the same subject. They are however collected at two different times separated with a time period which depends on the disorder which is at stake. For example, if the subject suffers from an inflammatory disease, the two samples can be collected with short time interval such as one-hour interval, two-hour interval, until one-day interval or one-week interval. If the subject suffers from cancer or a cardiovascular disease, then the time interval may be extended to a one-month interval, a two-month interval, etc. The skilled person will easily adjust said time interval to the situation he/she is facing.

By "disorder involving cell migration", it is herein included cancer, inflammatory diseases, and cardiovascular diseases.

Targeted cancers have been detailed above.

Inflammatory diseases include autoimmune syndromes and chronic inflammatory syndromes. Autoimmune syndromes are preferably selected from the group consisting of: ankylosing spondylitis, arthritis, rheumatoid arthritis, osteoarthritis, gout, Chagas disease, chronic obstructive pulmonary disease (COPD), dermatomyositis, diabetes mellitus type 1, endometriosis, Goodpasture's syndrome, Graves' disease, Guillain-Barre syndrome (GBS), Hashiomoto's disease, Hidradenitis suppurativa, Kawasaki disease, IgA nephropathy, Idiopathic thrombocytopenic purpura, inflammatory bowel disease, lupus, mixed connective tissue disease, morphea, multiple sclerosis, myasthenia gravis, narcolepsy, neuromyotonia, pemphigus vulgaris, pernicious anemia, psoriasis, psoriatic arthritis, polymyositis, primary biliary cirrhosis, relapsing polychondritis, schizophrenia, scleroderma, Sjogren's syndrome, Stiff person syndrome, temporal arteritis (also known as giant cell arteritis), vasculitis, vitiligo, and Wegener's granulomatosis. Chronic inflammatory syndromes are preferably selected from the group consisting of: asthma, rheumatoid arthritis, multiple sclerosis, psoriasis and Crohn's disease.

Cardiovascular diseases encompass diseases and disorders of the blood vessels of the heart, diseases and disorders of the vascular system, and/or diseases and disorders of organs and anatomical systems caused by the diseased condition of the vasculature. Examples include, but are not limited to: inflammation of the vasculature such as myocarditis, chronic autoimmune myocarditis, bacterial and viral myocarditis, as well as infective endocarditis; heart failure; congestive heart failure; chronic heart failure; cachexia of heart failure; cardiomyopathy, including non-ischemic (dilated cardiomyopathy; idiopathic dilated cardiomyopathy; cardiogenic shock, heart failure secondary to extracorporeal circulatory support ("post-pump syndrome"), heart failure following ischemia/reperfusion injury; hypertrophic cardiomyopathy; restrictive cardiomyopathy; non-ischemic systemic hypertension; valvular disease; arythmogenic right ventricular cardiomyopathy) and ischemic (atherogenesis; atherosclerosis; arteriosclerosis; peripheral vascular disease; coronary artery disease; infarctions, including stroke, transient ischemic attacks and myocardial infarctions). Additional disease states encompassed by the definition of cardiovascular disease include: aneurysms; arteritis; angina; embolism; platelet-associated ischemic disorders; ischemia/reperfusion injury; restenosis; mitral and/or tricuspid regurgitation; mitral stenosis; silent myocardial ischemia; Raynaud's phenomena; thrombosis; deep venous thrombosis; pulmonary embolism; thrombotic microangiopathies including thrombotic thrombocytopenic purpura (TTP) and hemolytic uremic syndrome (HUS), essential thrombocythemia, disseminated intravascular coagulation (DIC), and thrombosis and coagulopathies associated with exposure to a foreign or injured tissue surface-thrombophlebitis; vasculitis, including Kawasaki's vasculitis; Takayasu's arteritis; veno-occlusive disease, giant cell arteritis, Wegener's granulomatosis; Schoenlein-Henoch purpura, as well as cardiovascular disease arising from periodontal infections by one or more oral pathogens, such as bacteria. The examples of cardiovascular disease provided above are merely illustrative and provided to aid those of skill in the art to appreciate the scope of cardiovascular disease that can be prognosed by the methods of the invention.

It can be concluded from the method of the invention that, if the phosphorylation level of the biomarker of the invention in the second sample is superior to the phosphorylation level of said biomarker in the first sample, then the disorder worsens in the tested subject. This means, in other words, that the said disorder is likely to become more aggressive and that the said subject is not on the way of remission.

It can also mean that the treatment which has been administered so far to treat this disorder in said subject is not efficient and should be consequently adapted or changed.

In another aspect, the present invention thus relates to an in vitro method for controlling the efficiency of a treatment in a subject suffering from said disorder involving cell migration. Said method contains the same steps as the monitoring method of the invention described above. This method obviously requires that the said subject is currently treated by a determined treatment.

It results from this method that said treatment is diagnosed as "not efficient" in said subject if the phosphorylation level measured in said second sample is superior to the phosphorylation level measured in said first sample. In other words, it results from this method that the said subject is not responsive to said treatment.

The methods of the invention can be advantageously used to identify an efficient treatment for treating a subject suffering from a disorder involving cell migration. This can be achieved by reproducing the method for controlling the efficiency of a treatment as many times as necessary. In this case, the treatment to be tested can be also administered between the two sampling steps, so that the phosphorylation level of the biomarker of the invention before and after the administration of said treatment can be compared. Finally, it can be concluded that the tested treatment is to be replaced by a stronger one when the phosphorylation level measured in said second sample is superior to the phosphorylation level measured in said first sample.

Two different options can be foreseen when the current treatment is found inefficient: either the same treatment is maintained but its dosage regimen is revised (preferably enhanced), or the said treatment is supplemented or replaced with another existing treatment (if any).

For the first option, the Inventors propose to use the monitoring method of the invention for determining the efficient dose of the treatment to be administered in said non-responsive subject. In particular, it can be concluded from the results of the inventors that the dose of the said treatment is to be enhanced if the phosphorylation level measured in said second sample is superior to the phosphorylation level measured in said first sample. In the context of the invention, the appropriate dosage regimen will be identified once the phosphorylation level measured in said second sample will be similar or inferior to the phosphorylation level measured in said first sample.

For the second option, the Inventors propose to use the monitoring method of the invention for determining the treatment which is to be administered in said non-responsive subject in addition to or instead of the existing treatment. In particular, it can be concluded from the results of the inventors that the tested treatment (either the additional or the substitutive one) is not efficient enough as long as the phosphorylation level measured in said second sample is superior to the phosphorylation level measured in said first sample. In the context of the invention, the appropriate additional or substitutive treatment will be identified once the phosphorylation level measured in said second sample will be similar or inferior to the phosphorylation level measured in said first sample.

Of note, it is also encompassed in the present invention a method for treating a subject suffering from a disorder involving cell migration, said method comprising the steps of:
a) monitoring the evolution of a disorder according to the monitoring method of the invention, and
b) administering a treatment in said subject before or between the collection of said first and second samples,
wherein if the phosphorylation level measured in said second sample is superior to the phosphorylation level measured in said first sample, then the said treatment is not efficient in said subject.

Moreover, the present invention also encompasses a method for treating a subject suffering from a disorder involving cell migration, said method comprising the steps of:
a) controlling the efficiency of a treatment in a subject according to the method of the invention, and
b) administering to said subject an increased dose of the said treatment if the phosphorylation level measured in said second sample is superior to the phosphorylation level measured in said first sample, or
c) administering to said subject an additional treatment or a substitutive treatment if the phosphorylation level measured in said second sample is superior to the phosphorylation level measured in said first sample.

Optionally, the method for controlling the efficiency of a treatment in said subject may be reproduced in order to determine if the new dose or the new treatment is efficient in said subject.

By "increased dose", it is meant a dose which is superior to the dose which had been administered to the subject before the two biological samples were collected. This increase is dependent on the drug to be used and the skilled person will adjust it as recommended by their manufacturers.

Examples of suitable treatment for each kind of the targeted disorders are:
  Bevacizumab, sorafenib, sunitinib, vinblastine, taxol, or colchicine for treating cancer,
  Corticosteroids (such as corticosterone, cortisone, or aldosterone), azathioprine, mercaptopurine, infliximab, or adalimumab for treating inflammatory disorders,
  Propafenone, amiodarone, digoxine, fibrates (such as bezafibrate, fenofibrate, gemfibrozil), diazoxide, minoxidil for treating cardiovascular disorders.

The present Inventors identified for the first time that the RelB subunit of the NKKB pathway is phosphorylated on its serine 472 (or on a corresponding residue), so as to become activated and mediate the transactivation of many pro-migratory genes. This protein has been defined above as the "biomarker of the invention". Therefore, the present invention also relates to the said biomarker per se.

In particular, the present invention relates to an isolated RelB protein of SEQ ID NO:1 or an homolog thereof, which is phosphorylated at serine 472, or at a corresponding serine residue in said RelB homolog.

The definitions of the terms "homolog" and "corresponding residue" have been disclosed above.

The RelB protein may be synthetized by recombinant technologies that do not need to be herein detailed. The person skilled in the art may employ conventional molecular biology, microbiology and recombinant DNA techniques within the skill of the art. Such techniques are explained fully in the literature (see, for example, Sambrook, Fitsch & Maniatis, Molecular Cloning: A Laboratory Manual, Second Edition (1989) Cold Spring Harbor Laboratory Press, Cold Spring Harbor, N.Y. (referred to herein as "Sambrook et al., 1989").

The RelB phosphorylation of serine 472 or on a corresponding residue thereof may be achieved by contacting said RelB protein with an IκB kinase complex in phosphorylating conditions. The serine 472 will be specifically phosphorylated, as demonstrated in the example below.

Consequently, the present invention relates to a method to produce the said isolated protein, comprising the steps of a) providing a RelB protein of SEQ ID NO: 1 or an homolog thereof, and b) contacting said RelB protein with an IκB kinase complex in phosphorylating conditions.

Use of kinase assays by either immunoprecipitating endogenous IKK complex subunits (IKK immune complex kinase assay) or by using constitutively active IKK complex subunits (i.e., IKKα, IKKγ or IKKβ) are conventional for the skilled person. These kinase assays may be purchased by various biotech companies, such as Promega, Cell Signaling Technology, or Sigma-Aldrich. Phosphorylating conditions are described in the manufacturer instructions and in the examples below. They do not need to be detailed.

Finally, the present Inventors propose to use this isolated protein so as to identify potent antagonist of the RelB dependent—NFκB pathway in a screening method comprising the following steps:
a) providing a candidate molecule,
b) incubating the said candidate molecule with the RelB protein of SEQ ID NO:1 or an homolog thereof, in the presence of the IκB kinase in phosphorylating conditions, and
c) detecting whether phosphorylation of serine 472 in SEQ ID NO:1 or of a corresponding serine residue in a RelB homolog occurs.

Step c) of detection can be performed as mentioned above, for example by means of the reagent of the invention.

Phosphorylating conditions are disclosed in examples. Buffers can include for example 10 to 50 mM Hepes pH7.4 to pH7.6; 5 to 10 mM MgCl2; 10 to 100 μM ATP; 1.5 μg of either bacterially expressed GST alone (control) or of GST-RelB full length and mutant forms (as substrate). These reagents can be incubated at 30° C. for 25 min for allowing the phosphorylation to occur.

Similar kinase assays could be performed using whole cell extracts from transfected cells overexpressing either IKKα or IKKβ; or by using constitutively active IKKα or IKKβ kinases (purchased from Biotech companies).

The IkB kinase is for example supplied in convenient kits by Biotech suppliers such as Promega, Cell Signaling Technology, or Sigma-Aldrich.

Preferably, the screening method of the invention enables to identify molecule that prevents the phosphorylation of serine 472 of SEQ ID NO:1 or of the corresponding serine residue on said RelB homolog but not the phosphorylation of other serine in said proteins.

As Ser472-phosphorylated RelB has been associated with the development of cancer and inflammatory disease, such a candidate molecule may thus be an efficient anti-tumoral agent or an efficient anti-inflammatory agent. It is preferably a small chemical molecule. This molecule can be advantageously used in the treating methods of the invention mentioned above.

This screening method may also contain a step of detecting whether phosphorylation of other serine residue(s) in the RelB protein of SEQ ID NO:1 or in a RelB homolog occurs. The detection of these phosphorylated residue(s) may be performed by conventional antibodies such as the polyclonal RelB antibody Phospho-Ser$^{573}$ (Genscript; A00540-100); the RelB (Phospho-Ser$^{552}$) Antibody (#11255-2 of Signalway Antibody Co., Ltd); or #4999 of Cell Signaling Technology) (Leidner et al, *Oncogene* 2001).

Alternatively, this screening method may be based on the detection of the expression of the RelB-dependent pro-migratory genes that belong to the MMP family such as MMP3, MMP10, MMP12 or MMP9, as mentioned above.

EXAMPLES

Material and Methods
Antibodies and Reagent

The antibodies were purchased from Santa Cruz (RelB C19 # sc-226; IKKα M-204 # sc-7184 and Omniprobe M-21 # sc-499), Roche Applied Science (HA clone 3F10), Millipore (IKKβ clone 10AG2, #05-535,), BD Biosciences (IKK-γ # C73-764 and # C73-1794), Sigma-Aldrich (β-actin clone AC-15 # A5441), Life technologies (Rhodamine Phalloidin Conjugate, Molecular Probes®), and Eurogentec (custom phospho-RelB serine 472). Murine recombinant TNF-α was purchased from Sigma-Aldrich.
Production of Two Monoclonal Antibodies Specific for RelB-472SerP.

Four mice have been immunized by the injection of phosphorylated peptide (sequence: GTVS/(P03H2)/-LP-GLEPPG+C) coupled to KLH protein. Following three immunizations with this peptide and three boosts of, mouse lymphocytes from the spleen of the two best mice were fused with myeloma cells for hybridoma production. Positive hybridomas were screened first by ELISA comparing the signal with the non-phosphorylated vs the S472-phosphorylated peptide used for the immunization, and then by western blotting for detection of RelB S472 phosphorylation upon co-expression by transient transfection in 293 cells of the kinase IKKα along with either WT RelB or RelB S472A mutant. Two hybridomas out of thirty tested have been selected and entered the cloning phase. Further, ten subclones for each of the two hybridomas have been screened both by ELISA and western blotting as described above, and the two best subclones were selected for purification. The hybridoma producing one of these subclones was named RA3-AF3 and has been deposited at the Collection Nationale de Cultures de Microorganismes (CNCM) at the Institut Pasteur, 25, Rue du Docteur Roux, 75724 Paris, FR, on Nov. 18, 2020, under the deposit number CNCM 1-5612.
Plasmid Constructs Expression vectors for RelB were obtained from M. Körner (Institut André Lwoff, Villejuif, France), wild type and kinase inactive K44M mutants (KD) of HA-IKKα and HA-IKKβ were from M. Karin (University of California, San Diego, La Jolla, Calif.), and pSuper vector containing polymerase III H1 promoter was provided by T. Tuschl (The Rockfeller University, New-York, USA). pTRIP-RelB was generated by subcloning human full-length RelB cDNA into pTRIP-ΔU3-EF1α-IRES GFP lentiviral vector (Kieusseian et al, Blood 2006). GST-RelB full length and deletion mutants were obtained by subcloning RelB coding sequences from amino acids 1-580 (FL), 1-285 (N-ter), 271-580 (C-ter), 274-321 (Δ1), 316-377 (Δ2), 372-448 (Δ3), 441-504 (Δ4) and 499-580 (Δ5) following standard recombinant DNA procedures; and details are available upon request. GST-RelB point mutants were generated by substituting serine 451, 458, 468 and 472 to alanine using site-directed mutagenesis (QuickChange® kit, Qiagen) and confirmed by sequencing.
Cells Culture RelB-deficient mouse embryonic fibroblasts (MEFs) were kind gifts from F. Weih (Fritz Lipmann Institute, Jena, Germany). MEFs, HEK293 and 293T cells were grown in Dulbecco's modified Eagle medium (Life Technologies) supplemented with 10% heat-inactivated fetal bovine serum, 2 mM L-glutamine, 1 mM sodium pyruvate, 100 units/ml penicillin-streptomycin.
Kinase Assays For IKK immunocomplex kinase assays, whole cell extracts were prepared in whole cell lysis buffer (300 mM NaCl, 25 mM Hepes pH 7.7, 1.5 mM MgCl2, 0.2 mM EDTA, 0.5% triton supplemented with 10 mM p-nitrophenyl phosphate disodium salt, 20 mM β-glycerol phosphate, 100 μM Na3VO4, 1 mM PMSF, 1× complete protease inhibitor cocktail (Roche Diagnostic)). Either endogenous IKKα or -IKKβ or IKKγ/NEMO were immunoprecipitated from 100 μg of cell lysates with corresponding antibody for 2 h or overnight at 4° C., after which proteinA/G-agarose beads were added and incubation continued for 90 min at 4° C. The immunoprecipitates were collected, washed three times in lysis buffer and once in kinase buffer (20 mM Hepes pH7.6, 10 mM MgCl2), and then incubated at 30° C. for 25 min in 30 μl kinase reaction mixture containing 1 μCi γ$^{32}$P ATP, 1.5 μg of either bacterial expressed GST alone (control) or GST-RelB full length and mutant forms as substrate. The reaction was stopped by addition of an equal volume of Laemmli buffer and heat denaturation for 5 min at 90° C. Proteins were separated on 10% SDS-polyacrylamide gel and transferred to nitrocellulose membranes, stained with Ponceau S, subjected to autoradiography to visualize phosphorylated GST-fusion proteins, and finally analyzed by immunoblotting for normalization on amount of immunoprecipitated IKKs.
In Vivo Biotinylation Approach and Mass Spectrometry Analysis The approach was adapted from the method described by De Boer et al. based on efficient biotinylation in vivo and single-step purification of tagged transcription factors in mammalian cells (De Boer et al. *PNAS* 2003). Briefly, we first generated a lentiviral vector named pTRIP-BirA by subcloning the bacterial protein-biotin ligase BirA cDNA into the lentiviral vector pTRIP-ΔU3-EF1α-IRES GFP (Kieusseian et al, *Blood* 2006) and then subcloned the cDNA encoding full-length RelB tagged at the C-terminus by a peptide of 23 amino acids that can be biotinylated by BirA in vivo (RelB-BP). RelB-deficient MEFs were then stably transduced with either pTRIP-BirA empty vector or pTRIP-BirA expressing RelB-BP. Following large scale cell culture, cytoplasmic and nuclear extracts were incubated with streptavidin beads. Eluted proteins were separated by SDS-PAGE and then stained with colloidal blue. Each entire lane was divided into 2-3-mm gel slices (at least 20 gel plugs/lane) that were each treated by an in-gel-digested method using modified trypsin and further analyzed by nanoflow liquid chromatography-tandem coupled to a Q-TOF system (J. A. Demmers, Erasmus Medical Center, Rotterdam, The Netherlands). Data base searches were performed using MASCOT and Profound.

In Vivo Labeling and Phosphoamino Acid Analysis

Cells were either untreated or stimulated with TNFα for 6 hours and labeled with [$^{32}$P]-orthophosphate (0.5 mCi/mL) for the last 2 hours in phosphate-free DMEM. RelB was immunoprecipitated from whole cell extracts, separated by SDS-PAGE, and transferred to PVDF membrane. After visualization by autoradiography, RelB was revealed by immunoblotting on the same membrane. For phosphoamino acid analysis, metabolically labeled RelB was cut from the membrane, washed several times with water and hydrolyzed for 60 min at 110° C. in 6M HCl. The acid was evaporated and sample was dissolved in 10 µl of TLE pH 1,9 buffer (2.2% formic acid, 7.8% acetic acid) and mixed with 1 µg cold phosphoserine, phosphothreonine and phosphotyrosine standards. The location of the phosphoamino acids was mapped by ninhydrin staining and $^{32}$P radiolabeled phosphoamino acids were separated by single dimension thin layer electrophoresis and revealed by autoradiography as described previously (van der Geer P, Hunter T. (1994) *Electrophoresis.*).

Real Time RT-PCR

Total RNA extraction and RT were performed using TRIzol (Life Technologies) and Superscript VILO reverse transcriptase (Life Technologies), respectively. Real-time PCR analysis was carried out with LightCycler FastStart DNA Master$^{plus}$ SYBR Green I on a LightCycler 1.5 (Roche Applied Science). All values were normalized to the level of HPRT mRNA. Primers sequences are as follow: HPRT sense 5'-GCTGGTGAAAAGGACCTCT-3', HPRT antisense 5'CACAGGACTAGAACACCTGC-3'; MMP-3 sense 5'-CAGACTTGTCCCGTTTCCAT-3', MMP-3 antisense 5'-GGTGCTGACTGCATCAAAGA-3'.

Chromatin Immunoprecipitation (ChIP) Assays

ChIP assays were performed as described (Jacque et al, *Oncogene* 2012). Samples were analyzed by real-time PCR. Sequences of promoter-specific primers are as follow: MMP-3 sense 5'-CAGCCTGCTACTTAGTTCCTGTG-3', MMP-3 antisense 5'-CGACCACTTCTGCCCTGA-3' IκBα sense 5'-CGCTAAGAGGAACAGCCTAG-3', and IκBα sense 5'-GGAATTTCCAAGCCAGTCAG-3'.

MMP-3 Activity Assays

Cells ($3\times10^4$ cells/well) were seeded in 24-well plates and grown under the culture conditions as described above. Twenty-four hours later, cell culture supernatant was collected, incubated with 1 mM of 4-aminophenylmercuric acetate (APMA) for 24 hours at 37° C. to activate pro-MMPs, and MMP-3 activity measured by using the SensoLyte® 490 MMP-3 Fluorometric Assay Kit (AnaSpec) according to the manufacturer's instructions.

Scratch-Wound Assays

Cells ($2\times10^5$ cells/dish) seeded in 60 mm dishes were grown to confluent monolayer for 24 hours in DMEM with 10% FBS, after which FBS was lowered to 0,5% for an additional 24 hours before scratches were made simultaneously in all culture dishes using a 0.5 mm diameter pipette tip. Scratch area was monitored at the time of scratch (T0) and over 18 hours (T18). For TNFα induction studies, TNFα was added to serum-starved cell culture medium right after scratches were made. Quantification of wound closure was performed using the ImageJ software (http://rsbweb.nih.gov.ij/). Scratch wound results were compiled from seven dishes with one scratch in each dish.

Immunofluorescence Microscopy and Quantification of Actin Stress Fibers

Cells seeded on coverslips for 24 hours were fixed with 4% (w/v) paraformaldehyde in PBS for 20 min, washed once with PBS, and permeabilized for 5 min with 0.1% Triton X-100 in PBS at room temperature. After blocking with 10% FBS in PBS for 10 min at room temperature, cells were incubated with the Rhodamine Phalloidin Conjugate (1:200, Molecular Probes®) in 3% FBS in PBS for 20 min at room temperature. After two washes in PBS, the coverslips were mounted with Prolong Gold with DAPI (Life technologies). Fluorescence imaging was performed using a Zeiss Axio Observer D1 inverted microscope and a AxioCam MRC 3 camera using the AxioVision software (Carl Zeiss Imaging Solutions). The differences in actin stress fibers were quantified using the ImageJ software.

siRNA Transfections siRNA transfections were performed as described previously (Jacque et al, *PNAS*, 2005). All siRNA duplexes were synthesized by Sigma-Aldrich: siMMP-3#1 sense 5'-AA-GATTGTGTGTCGTTTATTAdTdT-3'; siMMP-3 #2 sense 5'-AAGATGTGAAGCAATTTATTAdTdT-3'; siRNA control sense 5'-CGUACGCGGAAUACUUCGAdTdT-3'.

Transwells 100 000 cells were seeded in 24-well transwell plates coated with matrigel (70 µl at 3 mg/ml). After an incubation at 37° C. for 24 hours, non-invaded cells on the top of the transwells were scraped off with a cotton swab, and invaded cells on the bottom of the transwells were fixed with ethanol for 10 min and stained with cristal violet 0.5%. Counting of invaded cells is performed by colorimetric assay at 560 nm on the cut off membrane placed in 100 µl of DMSO in a 96-well plate.

Immunohistochemistry Assays

Immunostaining was performed on a Leica-Bond automate using paraffin embedded cell pellets. After a pretreatment with ER1 buffer for 30 min followed by an incubation with primary antibodies at a 1/100 dilution for 20 min, the amplification and detection were performed using "Bond Polymer refine detection kit" (Leica), using immunoperoxidase conjugates and DAB as colorimetric substrate.

Statistical Analysis

Statistical significance was accessed using unpaired t tests (Prism 5.0c, GraphPad Software). A value of P<0.05 was considered as statistically significant with the following degrees: *P<0.05; P<0.01; *P<0.001.

Other Experimental Procedures

Transient transfections, lentiviral production and transduction, coimmunoprecipitation, immunoblotting, electromobility shift assays, and cell proliferation assays were all performed as described previously (Jacque et al, *PNAS*, 2005; Leotoing L. et al, *JBC*, 2011; Jacque et al, *Oncogene* 2012).

Results

The IKK Complex Binds to RelB in Fibroblasts

Although RelB was identified almost 30 years ago, little is known about its upstream activators and its downstream substrates. We identified IkB kinase (IKK) complex as a new RelB-interacting partner, this interaction was confirmed by coimmunoprecipitation experiments using whole cell extracts from WT MEFs either left untreated or treated by TNFα for 6 hours. As a control, similar immunoprecipitation experiments were performed by using nonimmune serum to verify the specificity of the interaction. Reciprocal experiments with RelB-, IKKα-, IKKβ- and NEMO-specific antibodies showed that endogenous RelB coimmunoprecipates with all three subunits of the IKK complex in resting and TNFα-induced cells. This result suggests that RelB interacts specifically and constitutively with the IKK complex.

Furthermore, beyond TNFα, RelB S472 phosphorylation occurs in response to another stimulus, lymphotoxin β. We have performed immunoblotting analysis of RelB-deficient MEF reexpressing either WT RelB or the RelB S472A mutant using anti-phospho serine-472 specific RelB antibody. Eight hours of lymphotoxinβ receptor stimulation led to a marked induction of RelB serine-472 phosphorylation in WT RelB expressing MEFs, whereas no such phosphorylation was observed in RelB S472A expressing cells (FIG. 1E). Importantly, RelB S472A-infected cell line expressed RelB at levels similar to that of WT RelB.

Given the ability of RelB to interact specifically with IKK, we hypothesized that IKK may directly control RelB activity by post-translational modifications. Five GST-RelB deletion mutants (noted Δ1-Δ5 mutants), each containing a subdomain of the RelB coding region, were used as substrates in IKKγ kinase assays (Δ1: amino acids 274-321 of SEQ ID NO:1; Δ2: amino acids 316-377 of SEQ ID NO:1; Δ3: amino acids 372-448 of SEQ ID NO:1; Δ4: amino acids 441-504 of SEQ ID NO:1; Δ5: amino acids 499-580 of SEQ ID NO:1). Only mutant Δ4 was efficiently phosphorylated by IKKγ. We have mutated each of the serine residues to alanine (S451A, S458A, S468A and S472A) into the Δ4 GST-RelB deletion mutant (FIG. 1A), and in vitro kinase assays revealed that only a point mutation at serine 472 abolished phosphorylation of the Δ4 RelB deletion mutant (FIG. 1B). Taken together, these results show that TNF-α induces in vitro the robust phosphorylation of RelB at serine 472 site by the complex IKK.

TNF-α Induces RelB Serine 472 Phosphorylation by IKK In Vivo

In vivo labeling experiments followed by RelB immunoprecipitation were performed with MEFs treated with TNF-α for 6 hours and showed that endogenous RelB is inducibly phosphorylated following TNF-α treatment. In order to examine the phosphorylation of endogenous RelB at serine 472, we have generated custom anti-phospho serine-472 specific RelB antibody and shown by immunoblotting that RelB serine-472 phosphorylation could be detected when WT RelB was coexpressed with HA-IKKα or HA-IKKβ but not catalytically inactive K44M IKKα and IKKβ mutants (FIG. 1C), indicating that a functional IKK complex is required for RelB-induced phosphorylation. Not surprisingly, no RelB phosphorylation was observed upon expression of the RelB S472A mutant.

Next, it was important to determine whether RelB serine-472 phosphorylation is increased by TNFα stimulation in vivo. A lentiviral vector was used to stably express human WT RelB or RelBS472A mutant in RelB-deficient MEFs. Six hours of TNFα stimulation led to a marked induction of RelB serine-472 phosphorylation, whereas no such phosphorylation was observed in RelB S472A expressing cells. Importantly, RelB S472A-infected cell line expressed RelB at levels similar to that of WT RelB and expression levels were similar to that of endogenous RelB in WT MEFs (FIG. 1D).

Those experiments confirmed that we identified RelB serine 472, which is conserved between mammals, as the main phosphorylation site in the transactivating C-terminus in vitro (FIG. 2).

Serine-472 Phosphorylation Status Regulates RelB Pro-Migration Function

As a role for RelB in cell motility and invasion has recently emerged in cancers cells, we speculated that inducible serine-472 phosphorylation of RelB might affect cell migration. We compared wound closure in RelB-deficient MEFs reconstituted with either an empty lentivirus or WT RelB or RelB S472A mutant either left untreated or stimulated with TNFα for 18 hours. As shown in FIGS. 3A and 3B, reintroduction of WT RelB but not S472A mutant markedly increased wound closure under the unstimulated conditions kinetics that parallel what is seen in noninfected WT MEFs, and remarkably the difference was even more pronounced at 18 hours post TNFα stimulation. We also shown that actin filament polymerization and remodeling are influenced by RelB S472 phosphorylation status as, upon TNFα treatment, reintroduction of WT RelB but not S472A RelB mutant markedly and significantly increased the number of stress fibers compared to that seen in empty lentivirus infected RelB-deficient MEFs (FIG. 4).

RelB Serine 472 Phosphorylation Status is Critical for TNF-α-Induced Expression of NF-κB Target Genes Involved in Cell Migration To gain further insights into the mechanisms that control the serine-472-dependent RelB activating function on fibroblast migration; we examined whether RelB serine-472 phosphorylation status has impact on RelB-mediated gene expression program, particularly those that could mediate the pro-migration function of RelB. We performed real-time RT-qPCR analysis on cDNA generated from reconstituted relb$^{-/-}$ MEFs treated with TNF-α for 8 hours and we determined for the first time the importance of RelB signaling in regulating Matrix Metalloproteinase such as MMP-3 and MMP-9 gene expression upon TNF-α treatment. Indeed, the expression of MMP-3 gene was strongly increased in the presence of RelB in MEFs treated with TNF-α and this induction was impaired in the S472A cells (FIG. 5A). This phospho-specific increase was not observed for other RelB-dependent genes such as Enpp2, CXCL12, PTX3, Snail or cIAP1 which were modulated upon introduction of WT RelB into RelB-deficient cells compared with what is seen in the empty virus-infected cells.

These results show that RelB exerts a serine 472-dependent selective activating function serving to control TNF-α-induced RelB activity. Further in vivo evidence for a direct role for RelB serine-472 phosphorylation in regulating MMP-3 transcription was obtained by chromatin immunoprecipitation (ChIP) analysis. As shown in FIG. 5B, TNFα stimulation induced efficient recruitment of WT RelB but not S472A mutant to the MMP-3 promoter. As a control, neither WT RelB nor S472A mutant were found to bind to the IκBα promoter. We next evaluated whether serine-472 of RelB is required for proper control of MMP-3 activity. MMP-3 activity was markedly and significantly increased upon TNFα stimulation in RelB-deficient MEFs infected with a lentivirus carrying WT RelB compared with what is seen in the empty virus-infected cells, whereas no such induction was found in S472A expressing cells (FIG. 5C). Taken together, these results suggest that TNFα-mediated RelB serine-472 phosphorylation up-regulates MMP-3 expression, and consequently its activity, through direct transcriptional control.

MMP-3 Activity is Critical for RelB Serine 472 in Promoting TNF-α-Induced Cell Migration in Fibroblasts Since we have characterized the pro-migration gene MMP-3 as a novel serine-472-dependent RelB target gene, we examined the direct contribution of MMP-3 in TNFα-induced RelB serine-472 mediated-cell migration by a direct RNA interference approach. We used two different siRNAs (siRNA MMP-3 #1 and siRNA MMP-3 #2) directed against MMP-3 to downregulate MMP-3 expression levels and addressed the effect of MMP-3 on cell migration in MEFs.

As shown in FIG. 6A, interfering with MMP-3 expression by siRNA abrogated TNF-α-enhanced migration of MEFs reconstituted with WT RelB, when compared with RelB-deficient MEFs or MEFs reconstituted with S472A form of RelB. We quantified the percentage of wound closure using ImageJ software and we showed that these differences in cell migration are statistically significant, notably following TNF-α stimulation (FIG. 6B). Importantly, these results demonstrate that MMP-3 inhibition significantly prevented the function of RelB S472 in promoting MEFs cell migration.

RelB Serine-472 Phosphorylation Status Regulates MMP3 Expression and RelB Pro-Migration Function in Breast Cancer Cells.

Strikingly, we revealed the requirement for RelB serine-472 in MDA-MB-231 invasive breast cancer cells in activating gene expression of MMP3, a member of the matrix metalloproteinase family with documented pro-migration and invasive function in cancer cells (FIG. 8A). As a control, DRAM1 mRNA expression levels appeared to be independent on RelB expression and its phosphorylation status on serine-472.

It was important to further explore the functional relevance of RelB serine-472 phosphorylation in metastatic breast cancer cells. We infected MDA-MB-231 cells with either an empty lentivirus or a lentivirus carrying WT RelB or the RelB S472A mutant. WT RelB ectopic expression had a modest but reproducible effect in increasing wound closure (30% vs 37%, n=2). Remarkably, expression of the S472A mutant markedly decreased wound closure compared to that seen in the empty vector control cells (30% vs 20%, n=2), thus indicating a dominant negative effect of RelB S472A mutant on pro-migration function of endogenous RelB (FIG. 8B).

Metastatic Breast Cancer Cell Lines Exhibit RelB Serine-472 Phosphorylation that is not Seen in Non-Metastatic Breast Cancer Cells.

We have performed immunoblotting analysis of 6 triple-negative basal-like highly invasive breast cancer cell lines vs 3 luminal A/B non-metastatic breast cancer cells using anti-phospho serine-472 specific RelB antibody. Remarkably, highly invasive basal-like breast cancer cells exhibit the highest level of RelB serine-472 phosphorylation (FIG. 9A). As a control, de-phosphorylated samples of MCF10A (FIG. 9B, left panels) and BT549 (FIG. 9B, right panels) exhibit no detectable signal, confirming phosphorylation as the nature of the detected band.

RelB Serine-472 Phosphorylation Promotes Invasion of Breast Cancer Cells

Next to study the role of RelB serine 472 in breast cancer cell invasion, we compared the invasion capacity of metastatic MDA-MB-231 breast cancer cells infected with either a lentivirus carrying WT RelB or the RelB S472A mutant by matrigel invasion assay. As shown in FIG. 10, expression of the S472A mutant markedly reduced the invasion of MDA-MB-231 cells compared to that seen in WT RelB expressing cells, thus indicating that RelB serine-472 phosphorylation promotes both breast cancer cell migration and invasion.

Validation of the Mouse Anti-Phospho Serine-472 Specific RelB Monoclonal Antibody by Immunohistochemistry (IHC) and Immunoblotting.

A monoclonal antibody directed against the phosphorylated form of RelB on S472 was generated and validated by IHC (FIG. 11A) and immunoblotting (FIG. 11B) on the invasive breast cancer MDA-MB-231 cells infected either with an empty lentivirus (control), or a lentivirus carrying WT RelB, or the RelB S472A mutant. As shown in FIG. 11A, a marked signal was detected upon ectopic expression of WT RelB but not S472A mutant in MDA-MB-231 cells. Similar results were obtained by immunoblotting (FIG. 11B).

Taken together, our data suggest that TNFα-induced serine-472 phosphorylation of RelB promotes cell migration by up-regulating selective RelB-gene expression program the expression of selective NF-κB target genes, such as MMP-3. Those results allow us to submit a novel molecular mechanism responsible for regulating cell migration through serine-472 phosphorylation of RelB (FIG. 7).

BIBLIOGRAPHIC REFERENCES

Attoub et al, *Journal of Medical Sciences*, Vol 3, No 1, 2010
Ausubel et al. CURRENT PROTOCOLS IN MOLECULAR BIOLOGY, 1989 Baud, V. & Karin, M. Signal transduction by tumor necrosis factor and its relatives. *Trends Cell Biol* 11, 372-7 (2001).
Bonizzi G, Bebien M, Otero D C, Johnson-Vroom K E, Cao Y, et al. (2004) Activation of IKKalpha target genes depends on recognition of specific kappaB binding sites by RelB:p52 dimers. Embo J 23: 4202-4210
Bonizzi, G. & Karin, M. The two NF-kappaB activation pathways and their role in innate and adaptive immunity. *Trends Immunol* 25, 280-8 (2004).
Chen, S Y; Bagley, J; Marasco, W A (1994). "Intracellular antibodies as a new class of therapeutic molecules for gene therapy". *Human gene therapy* 5 (5): 595-601.
Chow et al., *Cytometry (Communications in Clinical Cytometry)* 46: 72-78 (2001)
Claudio, E., Brown, K., Park, S., Wang, H. & Siebenlist, U. BAFF-induced NEMO-independent processing of NF-kappa B2 in maturing B cells. *Nat Immunol* 3, 958-65 (2002).
Conrad et al, *Methods Enzymol.* 267 (1996) 336-367
Coope, H. J. et al. CD40 regulates the processing of NF-kappaB2 p100 to p52. *Embo J* 21, 5375-85 (2002).
Derudder, E. et al. RelB/p50 dimers are differentially regulated by tumor necrosis factor-alpha and lymphotoxin-beta receptor activation. *J Biol Chem* 278, 23278-23284 (2003).
Curci J A, Liao S, Huffman M D, Shapiro S D, Thompson R W (December 1998). "Expression and localization of macrophage elastase (matrix metalloproteinase-12) in abdominal aortic aneurysms". *J. Clin. Invest.* 102 (11): 1900-10
Czernik, *Methods In Enzymology,* 201: 264-283 (1991)
De Boer E, Rodriguez P, Bonte E, Krijgsveld J, Katsantoni E, Heck A, Grosveld F, Strouboulis J. Proc Natl Acad Sci USA. 2003 Jun. 24; 100(13):7480-5.
Dejardin, E. The alternative NF-kappaB pathway from biochemistry to biology: pitfalls and promises for future drug development. *Biochem Pharmacol* 72, 1161-79 (2006).
Dejardin, E. et al. The lymphotoxin-beta receptor induces different patterns of gene expression via two NF-kappaB pathways. *Immunity* 17, 525-35 (2002).
Derudder E, Dejardin E, Pritchard L L, Green D R, Korner M, et al. (2003) RelB/p50 dimers are differentially regulated by tumor necrosis factor-alpha and lymphotoxin-beta receptor activation: critical roles for p100. J Biol Chem 278: 23278-23284
Ellington et Szostak, *Nature* 346 (6287) 1990), 818-822
Fusco A J, Huang D B, Miller D, Wang V Y, Vu D, et al. (2009) NF-kappaB p52:RelB heterodimer recognizes two classes of kappaB sites with two distinct modes. EMBO Rep 10: 152-159

Gerber et al. *PNAS* 100: 6940-5 (2003)

Ghosh, S. & Karin, M. Missing pieces in the NF-kappaB puzzle. *Cell* 109 Suppl, S81-96 (2002).

Guo, F., Kang, S., Zhou, P., Guo, L., Ma, L., and Hou, J. Maspin expression is regulated by the non-canonical NF-kappaB subunit in androgen-insensitive prostate cancer cell lines. Mol Immunol 49, 8-17. 2011

Hayden M S, Ghosh S. Shared principles in NF-kappaB signaling. Cell. 2008; 132(3):344-62.

Helbig G. et al, *J Biol Chem.* 2003 Jun. 13; 278(24):21631-8

Huse W, *Science* 246: 1275-81 (1989)

Jacque E, Tchenio T, Piton G, Romeo P H, Baud V. *Proc Natl Acad Sci USA.* 2005 Oct. 1; 102(41):14635-40.

Jacque E, Billot K, Authier H, Bordereaux D, Baud V. Oncogene. 2012 Jul. 9.

Justilien et al, Matrix Metalloproteinase-10 Is Required for Lung Cancer Stem Cell Maintenance, tumor Initiation and Metastatic Potential, *PLoS ONE*, vol 7, iss 4, e35040.

Kieusseian A, Chagraoui J, Kerdudo C, Mangeot P E, Gage P J, Navarro N, Izac B, Uzan G, Forget B G, Dubart-Kupperschmitt A. Blood. 2006 Jan. 15; 107(2):492-500.

Kohler and Milstein. *Nature* 265: 495-97 (1975)

Kohler and Milstein, *Eur. J. Immunol.* 6: 511 (1976)

Lee, D. W., Ramakrishnan, D., Valenta, J., Parney, I. F., Bayless, K. J., and Sitcheran, R. The NF-kappaB RelB Protein Is an Oncogenic Driver of Mesenchymal Glioma. PLoS One 8, e57489.

Julia Leidner, Lysann Palkowitsch, Ralf Marienfeld, The phosphorylation at threonine 84 and serine 552 regulates the activity of the NF-kappaB transcription factor RelB Oncogene. 2001 Dec. 6; 20(56):8142-7.

Leotoing L, Chereau F, Baron S, Hube F, Valencia H J, Bordereaux D, Demmers J A, Strouboulis J, Baud V. *J Biol Chem.* 2011 Sep. 16; 286(37):32277-88.

McCauley et al, *Analytical Biochemistry* 319 (2003) 244-250

Maier H J, Marienfeld R, Wirth T, Baumann B (2003) Critical role of RelB serine 368 for dimerization and p100 stabilization. J Biol Chem 278: 39242-39250

Mann M., Shao-En Ong, Mads Grønborg, Hanno Steen, Ole N. Jensen and Akhilesh Pandey, Analysis of protein phosphorylation using mass spectrometry: deciphering the phosphoproteome *TRENDS in Biotechnology* Vol. 20 No. 6 Jun. 2002 Marienfeld R, May M J, Berberich I, Serfling E, Ghosh S, et al. (2003) RelB forms transcriptionally inactive complexes with RelA/p65. J Biol Chem 278: 19852-19860

Marienfeld R, Berberich-Siebelt F, Berberich I, Denk A, Serfling E, Neumann M (2001) Signal-specific and phosphorylation-dependent RelB degradation: a potential mechanism of NF-kappaB control. Oncogene., 20:8142-7.

Merrifield, *J. Am. Chem. Soc.* 85: 21-49 (1962)

Mhashilkar, A M; Bagley, J; Chen, S Y; Szilvay, A M; Helland, D G; Marasco, W A (1995). "Inhibition of HIV-1 Tat-mediated LTR transactivation and HIV-1 infection by anti-Tat single chain intra bodies". *The EMBO Journal* 14 (7): 1542-51.

Monaco et al, *Proc Natl Acad Sci USA.* 2004 Apr. 13; 101(15):5634-9

Mullinax et al., *PNAS* 1990 October; 87(20):8095-9.

Natoli G, De Santa F (2006) Shaping alternative NF-kappaB-dependent gene expression programs: new clues to specificity. Cell Death Differ 13: 693-696

Needleman and Wunsch *J. Mol. Biol.* 1970 March; 48(3): 443-53.

Neuberger et al., *Nature* 312: 604 (1984)

Oeckinghaus A, Ghosh S. The NF-kappaB family of transcription factors and its regulation. Cold Spring Harb Perspect Biol. 2009; 1(4):a000034.

Rhee et al, *Journal of Biochemistry and Molecular Biology*, 2007 Jan. 31; 40(1):88-94

Rinaldi et al, The use of fluorescent intrabodies to detect endogenous gankyrin in living cancer cells, Exp Cell Res. 2013 Apr. 1; 319(6):838-49

Saccani S, Pantano S, Natoli G (2003) Modulation of NF-kappaB activity by exchange of dimers. Mol Cell 11: 1563-1574

Spira et al., *J. Immunol. Methods,* 74: 307 (1984)

Steplewski, et al., *PNAS,* 82: 8653 (1985)

Sun et al, *Carcinogenesis,* 2012 April; 33(4):810-7.

Tatusova et al., «Blast 2 sequences—a new tool for comparing protein and nucleotide sequences», *FEMS Microbiol.,* 1999 May 15; 174(2):247-50

Van der Geer P, Hunter T. (1994) *Electrophoresis.* March-April; 15(3-4):544-54

Wang X, Belguise K, Kersual N, Kirsch K H, Mineva N D, Galtier F, Chalbos D, Sonenshein G E Oestrogen signalling inhibits invasive phenotype by repressing RelB and its target BCL2. Nat Cell Biol. 2007 April; 9(4):470-8.

Wang, X., Belguise, K., O'Neill, C. F., Sanchez-Morgan, N., Romagnoli, M., Eddy, S. F., Mineva, N. D., Yu, Z., Min, C., Trinkaus-Randall, V., et al. (2009). RelB NF-kappaB represses estrogen receptor alpha expression via induction of the zinc finger protein Blimp1. Mol Cell Biol 29, 3832-3844.

Woodruff P G, Koth L L, Yang Y H, Rodriguez M W, Favoreto S, Dolganov G M, Paquet A C, Erle D J (December 2005). "A Distinctive Alveolar Macrophage Activation State Induced by Cigarette Smoking". *Am. J. Respir. Crit. Care Med.* 172 (11): 1383-92

Xiao, G., Harhaj, E. W. & Sun, S. NF-kappaB-Inducing Kinase Regulates the Processing of NF-kappaB2 p100. *Mol Cell* 7, 401-409. (2001).

Yilmaz Z B, Weih D S, Sivakumar V, Weih F (2003) RelB is required for Peyer's patch development: differential regulation of p52-RelB by lymphotoxin and TNF. *Embo J* 22: 121-130

The invention claimed is:

1. The monoclonal antibody produced by hybridoma RA3-AF3, deposited at the Collection Nationale de Cultures de Microorganismes (CNCM) at the Institut Pasteur, 25, Rue du Docteur Roux, 75724 Paris, FR, on Nov. 18, 2020, under the deposit number CNCM I-5612.

2. A method, comprising:
   a) providing a sample;
   b) contacting the sample with the monoclonal antibody of claim 1; and
   c) detecting binding between the monoclonal antibody and RelB (SEQ ID NO: 1) phosphorylated on serine 472 or a RelB-homologue having at least 80% identity to (SEQ ID NO: 1) and phosphorylated on a corresponding serine, in said sample.

3. The method of claim 2, wherein binding between the monoclonal antibody and RelB (SEQ ID NO: 1) phosphorylated on serine 472 is detected.

* * * * *

SEQUENCE LISTING

```
<160> NUMBER OF SEQ ID NOS: 9

<210> SEQ ID NO 1
<211> LENGTH: 579
<212> TYPE: PRT
<213> ORGANISM: Homo Sapiens
<220> FEATURE:
<221> NAME/KEY: MISC_FEATURE
<223> OTHER INFORMATION: RelB Human
```

<400> SEQUENCE: 1

```
Met Leu Arg Ser Gly Pro Ala Ser Gly Pro Ser Val Pro Thr Gly Arg
1               5                   10                  15

Ala Met Pro Ser Arg Arg Val Ala Arg Pro Pro Ala Ala Pro Glu Leu
            20                  25                  30

Gly Ala Leu Gly Ser Pro Asp Leu Ser Ser Leu Ser Leu Ala Val Ser
        35                  40                  45

Arg Ser Thr Asp Glu Leu Glu Ile Ile Asp Glu Tyr Ile Lys Glu Asn
    50                  55                  60

Gly Phe Gly Leu Asp Gly Gly Gln Pro Gly Pro Gly Glu Gly Leu Pro
65                  70                  75                  80

Arg Leu Val Ser Arg Gly Ala Ala Ser Leu Ser Thr Val Thr Leu Gly
                85                  90                  95

Pro Val Ala Pro Pro Ala Thr Pro Pro Pro Trp Gly Cys Pro Leu Gly
            100                 105                 110

Arg Leu Val Ser Pro Ala Pro Gly Pro Gly Pro Gln Pro His Leu Val
        115                 120                 125

Ile Thr Glu Gln Pro Lys Gln Arg Gly Met Arg Phe Arg Tyr Glu Cys
    130                 135                 140

Glu Gly Arg Ser Ala Gly Ser Ile Leu Gly Glu Ser Ser Thr Glu Ala
145                 150                 155                 160

Ser Lys Thr Leu Pro Ala Ile Glu Leu Arg Asp Cys Gly Gly Leu Arg
                165                 170                 175

Glu Val Glu Val Thr Ala Cys Leu Val Trp Lys Asp Trp Pro His Arg
            180                 185                 190

Val His Pro His Ser Leu Val Gly Lys Asp Cys Thr Asp Gly Ile Cys
        195                 200                 205

Arg Val Arg Leu Arg Pro His Val Ser Pro Arg His Ser Phe Asn Asn
    210                 215                 220

Leu Gly Ile Gln Cys Val Arg Lys Lys Glu Ile Glu Ala Ala Ile Glu
225                 230                 235                 240

Arg Lys Ile Gln Leu Gly Ile Asp Pro Tyr Asn Ala Gly Ser Leu Lys
                245                 250                 255

Asn His Gln Glu Val Asp Met Asn Val Val Arg Ile Cys Phe Gln Ala
            260                 265                 270

Ser Tyr Arg Asp Gln Gln Gly Gln Met Arg Arg Met Asp Pro Val Leu
        275                 280                 285

Ser Glu Pro Val Tyr Asp Lys Lys Ser Thr Asn Thr Ser Glu Leu Arg
    290                 295                 300

Ile Cys Arg Ile Asn Lys Glu Ser Gly Pro Cys Thr Gly Gly Glu Glu
305                 310                 315                 320

Leu Tyr Leu Leu Cys Asp Lys Val Gln Lys Glu Asp Ile Ser Val Val
                325                 330                 335

Phe Ser Arg Ala Ser Trp Glu Gly Arg Ala Asp Phe Ser Gln Ala Asp
            340                 345                 350

Val His Arg Gln Ile Ala Ile Val Phe Lys Thr Pro Pro Tyr Glu Asp
        355                 360                 365

Leu Glu Ile Val Glu Pro Val Thr Val Asn Val Phe Leu Gln Arg Leu
    370                 375                 380

Thr Asp Gly Val Cys Ser Glu Pro Leu Pro Phe Thr Tyr Leu Pro Arg
385                 390                 395                 400

Asp His Asp Ser Tyr Gly Val Asp Lys Lys Arg Lys Arg Gly Met Pro
```

```
                    405                 410                 415
Asp Val Leu Gly Glu Leu Asn Ser Ser Asp Pro His Gly Ile Glu Ser
                420                 425                 430

Lys Arg Arg Lys Lys Pro Ala Ile Leu Asp His Phe Leu Pro Asn
            435                 440                 445

His Gly Ser Gly Pro Phe Leu Pro Pro Ser Ala Leu Leu Pro Asp Pro
450                 455                 460

Asp Phe Phe Ser Gly Thr Val Ser Leu Pro Gly Leu Glu Pro Pro Gly
465                 470                 475                 480

Gly Pro Asp Leu Leu Asp Asp Gly Phe Ala Tyr Asp Pro Thr Ala Pro
                485                 490                 495

Thr Leu Phe Thr Met Leu Asp Leu Leu Pro Ala Pro Pro His Ala
            500                 505                 510

Ser Ala Val Val Cys Ser Gly Gly Ala Gly Ala Val Val Gly Glu Thr
                515                 520                 525

Pro Gly Pro Glu Pro Leu Thr Leu Asp Ser Tyr Gln Ala Pro Gly Pro
                530                 535                 540

Gly Asp Gly Gly Thr Ala Ser Leu Val Gly Ser Asn Met Phe Pro Asn
545                 550                 555                 560

His Tyr Arg Glu Ala Ala Phe Gly Gly Gly Leu Leu Ser Pro Gly Pro
                565                 570                 575

Glu Ala Thr

<210> SEQ ID NO 2
<211> LENGTH: 558
<212> TYPE: PRT
<213> ORGANISM: Mus Musculus
<220> FEATURE:
<221> NAME/KEY: MISC_FEATURE
<223> OTHER INFORMATION: RelB MusMusculus

<400> SEQUENCE: 2

Met Pro Ser Arg Arg Ala Ala Arg Glu Ser Ala Pro Glu Leu Gly Ala
1               5                   10                  15

Leu Gly Ser Ser Asp Leu Ser Ser Leu Ser Leu Thr Val Ser Arg Thr
                20                  25                  30

Thr Asp Glu Leu Glu Ile Ile Asp Glu Tyr Ile Lys Glu Asn Gly Phe
            35                  40                  45

Gly Leu Asp Gly Thr Gln Leu Ser Glu Met Pro Arg Leu Val Pro Arg
        50                  55                  60

Gly Pro Ala Ser Leu Ser Ser Val Thr Leu Gly Pro Ala Ala Pro Pro
65                  70                  75                  80

Pro Pro Ala Thr Pro Ser Trp Ser Cys Thr Leu Gly Arg Leu Val Ser
                85                  90                  95

Pro Gly Pro Cys Pro Arg Pro Tyr Leu Val Ile Thr Glu Gln Pro Lys
                100                 105                 110

Gln Arg Gly Met Arg Phe Arg Tyr Glu Cys Glu Gly Arg Ser Ala Gly
            115                 120                 125

Ser Ile Leu Gly Glu Ser Ser Thr Glu Ala Ser Lys Thr Leu Pro Ala
        130                 135                 140

Ile Glu Leu Arg Asp Cys Gly Gly Leu Arg Glu Val Glu Val Thr Ala
145                 150                 155                 160

Cys Leu Val Trp Lys Asp Trp Pro His Arg Val His Pro His Ser Leu
                165                 170                 175

Val Gly Lys Asp Cys Thr Asp Gly Val Cys Arg Val Arg Leu Arg Pro
```

```
            180                 185                 190
His Val Ser Pro Arg His Ser Phe Asn Asn Leu Gly Ile Gln Cys Val
                195                 200                 205

Arg Lys Lys Glu Ile Glu Ala Ala Ile Glu Arg Lys Ile Gln Leu Gly
210                 215                 220

Ile Asp Pro Tyr Asn Ala Gly Ser Leu Lys Asn His Gln Glu Val Asp
225                 230                 235                 240

Met Asn Val Val Arg Ile Cys Phe Gln Ala Ser Tyr Arg Asp Gln Gln
                245                 250                 255

Gly His Leu His Arg Met Asp Pro Ile Leu Ser Glu Pro Val Tyr Asp
            260                 265                 270

Lys Lys Ser Thr Asn Thr Ser Glu Leu Arg Ile Cys Arg Ile Asn Lys
                275                 280                 285

Glu Ser Gly Pro Cys Thr Gly Gly Glu Glu Leu Tyr Leu Leu Cys Asp
            290                 295                 300

Lys Val Gln Lys Glu Asp Ile Ser Val Val Phe Ser Thr Ala Ser Trp
305                 310                 315                 320

Glu Gly Arg Ala Asp Phe Ser Gln Ala Asp Val His Arg Gln Ile Ala
                325                 330                 335

Ile Val Phe Lys Thr Pro Pro Tyr Glu Asp Leu Glu Ile Ser Glu Pro
            340                 345                 350

Val Thr Val Asn Val Phe Leu Gln Arg Leu Thr Asp Gly Val Cys Ser
            355                 360                 365

Glu Pro Leu Pro Phe Thr Tyr Leu Pro Arg Asp His Asp Ser Tyr Gly
    370                 375                 380

Val Asp Lys Lys Arg Lys Arg Gly Leu Pro Asp Val Leu Gly Glu Leu
385                 390                 395                 400

Ser Ser Ser Asp Pro His Gly Ile Glu Ser Lys Arg Arg Lys Lys Lys
                405                 410                 415

Pro Val Phe Leu Asp His Phe Leu Pro Gly His Ser Ser Gly Leu Phe
            420                 425                 430

Leu Pro Pro Ser Ala Leu Gln Pro Ala Asp Ser Asp Phe Phe Pro Ala
            435                 440                 445

Ser Ile Ser Leu Pro Gly Leu Glu Pro Gly Gly Pro Asp Leu Leu
            450                 455                 460

Asp Asp Gly Phe Ala Tyr Asp Pro Ser Ala Pro Thr Leu Phe Thr Met
465                 470                 475                 480

Leu Asp Leu Leu Pro Pro Ala Pro Pro Leu Ala Ser Ala Val Val Gly
                485                 490                 495

Ser Gly Gly Ala Gly Ala Thr Val Val Glu Ser Ser Gly Pro Glu Pro
            500                 505                 510

Leu Ser Leu Asp Ser Phe Ala Ala Pro Gly Pro Gly Asp Val Gly Thr
            515                 520                 525

Ala Ser Leu Val Gly Ser Asn Met Phe Pro Asn Gln Tyr Arg Glu Ala
            530                 535                 540

Ala Phe Gly Gly Gly Leu Leu Ser Pro Gly Pro Glu Ala Thr
545                 550                 555

<210> SEQ ID NO 3
<211> LENGTH: 607
<212> TYPE: PRT
<213> ORGANISM: Rattus Norvegicus
<220> FEATURE:
<221> NAME/KEY: MISC_FEATURE
<223> OTHER INFORMATION: RelB Rattus Norvegicus
```

```
<400> SEQUENCE: 3

Met Met Pro Arg Ala Pro Cys Val Gln Pro Gly Leu Arg Pro Tyr Pro
1               5                   10                  15

Cys Ala Ala Ser Pro Ala Gly Asp Arg Pro Asn Arg Leu Gly Cys Pro
            20                  25                  30

Ala Ala Arg Leu Ala Leu Val Arg Ala Arg Pro Glu Leu Ala Phe Gly
        35                  40                  45

Leu Ser Val Pro Thr Gly Arg Ala Met Pro Ser Arg Ala Ala Arg
    50                  55                  60

Glu Ser Ala Pro Glu Leu Gly Ala Leu Gly Ser Ser Asp Ile Pro Ser
65                  70                  75                  80

Leu Ser Arg Thr Thr Glu Ile Ile Asp Glu Tyr Ile Lys Glu Asn Gly
                85                  90                  95

Phe Gly Leu Asp Gly Ala Gln Leu Ser Glu Met Pro Arg Leu Val Pro
                100                 105                 110

Arg Gly Pro Ala Ser Leu Ser Ser Val Thr Leu Gly Pro Ala Ala Pro
            115                 120                 125

Pro Pro Pro Ala Thr Pro Pro Trp Asn Cys Thr Leu Gly Arg Leu Val
130                 135                 140

Ser Pro Gly Pro Cys Pro Arg Pro Tyr Leu Val Ile Thr Glu Gln Pro
145                 150                 155                 160

Lys Gln Arg Gly Met Arg Phe Arg Tyr Glu Cys Glu Gly Arg Ser Ala
                165                 170                 175

Gly Ser Ile Leu Gly Glu Ser Ser Thr Glu Ala Ser Lys Thr Leu Pro
                180                 185                 190

Ala Ile Glu Leu Arg Asp Cys Gly Gly Leu Arg Glu Val Glu Val Thr
            195                 200                 205

Ala Cys Leu Val Trp Lys Asp Trp Pro His Arg Val His Pro His Ser
210                 215                 220

Leu Val Gly Lys Asp Cys Thr Asp Gly Val Cys Arg Val Arg Leu Arg
225                 230                 235                 240

Pro His Val Ser Pro Arg His Ser Phe Asn Asn Leu Gly Ile Gln Cys
                245                 250                 255

Val Arg Lys Lys Glu Ile Glu Ala Ala Ile Glu Arg Lys Ile Gln Leu
                260                 265                 270

Gly Ile Asp Pro Tyr Asn Ala Gly Ser Leu Lys Asn His Gln Glu Val
            275                 280                 285

Asp Met Asn Val Val Arg Ile Cys Phe Gln Ala Ser Tyr Arg Asp Gln
290                 295                 300

Gln Gly His Leu His Arg Met Asp Pro Ile Leu Ser Glu Pro Val Tyr
305                 310                 315                 320

Asp Lys Lys Ser Thr Asn Thr Ser Glu Leu Arg Ile Cys Arg Ile Asn
                325                 330                 335

Lys Glu Ser Gly Pro Cys Thr Gly Gly Glu Glu Leu Tyr Leu Leu Cys
            340                 345                 350

Asp Lys Val Gln Lys Glu Asp Ile Ser Val Val Phe Ser Thr Ala Ser
                355                 360                 365

Trp Glu Gly Arg Ala Asp Phe Ser Gln Ala Asp Val His Arg Gln Ile
            370                 375                 380

Ala Ile Val Phe Lys Thr Pro Pro Tyr Glu Asp Leu Glu Ile Ser Glu
385                 390                 395                 400

Pro Val Thr Val Asn Val Phe Leu Gln Arg Leu Thr Asp Gly Val Cys
```

```
            405                 410                 415
Ser Glu Pro Leu Pro Phe Thr Tyr Leu Pro Arg Asp His Asp Ser Tyr
            420                 425                 430

Gly Val Asp Lys Lys Arg Lys Arg Gly Leu Pro Asp Val Leu Gly Glu
            435                 440                 445

Leu Ser Ser Ser Asp Pro His Gly Ile Glu Ser Lys Arg Arg Lys Lys
450                 455                 460

Lys Pro Val Phe Leu Asp His Phe Leu Pro Gly His Ser Ser Gly Leu
465                 470                 475                 480

Phe Leu Pro Pro Ser Ala Leu Gln Ser Ala Asp Thr Asp Phe Phe Pro
            485                 490                 495

Gly Thr Ile Ser Leu Pro Gly Leu Glu Pro Pro Gly Gly Pro Asp Leu
            500                 505                 510

Leu Asp Asp Gly Phe Ala Tyr Asp Pro Ser Ala Pro Thr Leu Phe Thr
            515                 520                 525

Met Leu Asp Leu Leu Pro Pro Ala Pro Pro Leu Ala Ser Ala Val Val
            530                 535                 540

Gly Asn Gly Gly Ala Gly Ala Thr Val Val Glu Ser Pro Gly Pro Glu
545                 550                 555                 560

Pro Leu Ser Leu Asp Ser Phe Ala Ala Pro Gly Pro Gly Asp Val Gly
            565                 570                 575

Thr Ala Ser Leu Val Gly Ser Asn Met Phe Pro Asn Gln Tyr Arg Glu
            580                 585                 590

Ala Ala Phe Gly Gly Gly Leu Leu Ser Pro Gly Pro Glu Ala Thr
            595                 600                 605

<210> SEQ ID NO 4
<211> LENGTH: 647
<212> TYPE: PRT
<213> ORGANISM: Bos Taurus
<220> FEATURE:
<221> NAME/KEY: MISC_FEATURE
<223> OTHER INFORMATION: RelB Bos Taurus

<400> SEQUENCE: 4

Met Asn Ala Gln Ala Gly Gly Ala Gly Glu Phe Arg Arg Pro Ala Pro
1               5                   10                  15

Ala Arg Arg Pro Pro Gly Pro Ala Arg Arg Pro Pro Gln Pro Arg Ala
            20                  25                  30

Pro Arg Val Gln Pro Gly Leu Arg Pro Gln Pro Leu Arg Arg Ser Pro
            35                  40                  45

Asp Pro Arg Ser Ser Ala Arg Pro Cys His Leu Ala Ala Leu Pro Ala
        50                  55                  60

Arg Val Cys Val Phe Trp Ser Gly Leu Ala Ser Gly Pro Ser Val Pro
65                  70                  75                  80

Thr Gly Trp Ala Met Pro Ser Arg Arg Val Ala Arg Ser Ser Ala Ala
            85                  90                  95

Pro Glu Leu Gly Pro Leu Gly Ser Ala Asp Leu Ser Ser Leu Ser Leu
            100                 105                 110

Ala Val Ser Arg Thr Thr Asp Glu Leu Glu Ile Ile Asp Glu Tyr Ile
            115                 120                 125

Lys Glu Asn Gly Phe Gly Leu Glu Gly Ala Gln Pro Gly Pro Glu Gly
        130                 135                 140

Leu Pro Arg Leu Val Ser Arg Gly Ala Ala Ser Leu Ser Thr Val Thr
145                 150                 155                 160
```

```
Leu Gly Pro Ala Ala Pro Pro Pro Ala Thr Pro Pro Trp Gly
            165                 170                 175
Cys Thr Leu Gly Arg Leu Val Pro Pro Ala Gly Ala Gly Pro Arg
            180                 185                 190
Pro His Leu Val Ile Thr Glu Gln Pro Lys Gln Arg Gly Met Arg Phe
            195                 200                 205
Arg Tyr Glu Cys Glu Gly Arg Ser Ala Gly Ser Ile Leu Gly Glu Ser
            210                 215                 220
Ser Thr Glu Ala Ser Lys Thr Leu Pro Ala Ile Glu Leu Arg Asp Cys
225                 230                 235                 240
Gly Gly Leu Arg Glu Val Glu Val Thr Ala Cys Leu Val Trp Lys Asp
            245                 250                 255
Trp Pro His Arg Val His Pro His Ser Leu Val Gly Lys Asp Cys Thr
            260                 265                 270
Asp Gly Val Cys Arg Val Arg Leu Arg Pro His Val Ser Pro Arg His
            275                 280                 285
Ser Phe Asn Asn Leu Gly Ile Gln Cys Val Arg Lys Lys Glu Ile Glu
            290                 295                 300
Ala Ala Ile Glu Arg Lys Ile Gln Leu Gly Ile Asp Pro Tyr Asn Ala
305                 310                 315                 320
Gly Ser Leu Lys Asn His Gln Glu Val Asp Met Asn Val Val Arg Ile
            325                 330                 335
Cys Phe Gln Ala Ser Tyr Arg Asp Gln Gln Gly Gln Met Arg Arg Met
            340                 345                 350
Asp Pro Val Leu Ser Glu Pro Val Tyr Asp Lys Lys Ser Thr Asn Thr
            355                 360                 365
Ser Glu Leu Arg Ile Cys Arg Ile Asn Lys Glu Ser Gly Pro Cys Thr
            370                 375                 380
Gly Gly Glu Glu Leu Tyr Leu Leu Cys Asp Lys Val Gln Lys Glu Asp
385                 390                 395                 400
Ile Ser Val Val Phe Ser Arg Ala Ser Trp Glu Gly Arg Ala Asp Phe
            405                 410                 415
Ser Gln Ala Asp Val His Arg Gln Ile Ala Ile Val Phe Lys Thr Pro
            420                 425                 430
Pro Tyr Glu Asp Leu Glu Ile Val Glu Pro Val Thr Val Asn Val Phe
            435                 440                 445
Leu Gln Arg Leu Thr Asp Gly Val Cys Ser Glu Pro Leu Pro Phe Thr
            450                 455                 460
Tyr Leu Pro Arg Asp His Asp Ser Tyr Gly Val Asp Lys Lys Arg Lys
465                 470                 475                 480
Arg Gly Leu Pro Asp Val Leu Gly Glu Leu Asn Ser Ser Asp Pro His
            485                 490                 495
Gly Ile Glu Ser Lys Arg Arg Lys Lys Pro Val Phe Leu Asp Gln
            500                 505                 510
Phe Leu Pro Ser His Gly Ser Gly Pro Tyr Leu Pro Ser Val Leu
            515                 520                 525
Leu Pro Asp Thr Asp Phe Tyr Pro Gly Thr Val Ser Leu Pro Ser Leu
            530                 535                 540
Glu Pro Pro Gly Gly Pro Asp Leu Leu Asp Asp Ser Phe Pro Tyr Asp
545                 550                 555                 560
Pro Ala Ala Pro Thr Leu Leu Thr Met Leu Asp Met Leu Pro Pro Ala
            565                 570                 575
Pro Pro Leu Thr Ser Ala Val Ala Gly Asn Gly Gly Ala Gly Ala Ala
```

```
                580             585             590
Val Gly Glu Pro Pro Gly Pro Glu Pro Leu Thr Leu Asp Ser Tyr Gln
            595             600             605

Ala Pro Gly Pro Gly Asp Gly Gly Thr Ala Ser Leu Val Gly Ser Asn
            610             615             620

Met Phe Pro Asn Gln Tyr Arg Glu Ala Gly Phe Gly Gly Gly Leu Leu
625             630             635             640

Ser Pro Gly Pro Glu Ala Thr
            645

<210> SEQ ID NO 5
<211> LENGTH: 13
<212> TYPE: PRT
<213> ORGANISM: artificial
<220> FEATURE:
<223> OTHER INFORMATION: RelB immunogenic peptide

<400> SEQUENCE: 5

Gly Thr Val Ser Leu Pro Gly Leu Glu Pro Pro Gly Gly
1               5                   10

<210> SEQ ID NO 6
<211> LENGTH: 477
<212> TYPE: PRT
<213> ORGANISM: Homo Sapiens
<220> FEATURE:
<221> NAME/KEY: MISC_FEATURE
<223> OTHER INFORMATION: MMP3 Homo Sapiens

<400> SEQUENCE: 6

Met Lys Ser Leu Pro Ile Leu Leu Leu Leu Cys Val Ala Val Cys Ser
1               5                   10                  15

Ala Tyr Pro Leu Asp Gly Ala Ala Arg Gly Glu Asp Thr Ser Met Asn
            20                  25                  30

Leu Val Gln Lys Tyr Leu Glu Asn Tyr Tyr Asp Leu Lys Lys Asp Val
        35                  40                  45

Lys Gln Phe Val Arg Arg Lys Asp Ser Gly Pro Val Val Lys Lys Ile
    50                  55                  60

Arg Glu Met Gln Lys Phe Leu Gly Leu Glu Val Thr Gly Lys Leu Asp
65                  70                  75                  80

Ser Asp Thr Leu Glu Val Met Arg Lys Pro Arg Cys Gly Val Pro Asp
                85                  90                  95

Val Gly His Phe Arg Thr Phe Pro Gly Ile Pro Lys Trp Arg Lys Thr
            100                 105                 110

His Leu Thr Tyr Arg Ile Val Asn Tyr Thr Pro Asp Leu Pro Lys Asp
        115                 120                 125

Ala Val Asp Ser Ala Val Glu Lys Ala Leu Lys Val Trp Glu Glu Val
    130                 135                 140

Thr Pro Leu Thr Phe Ser Arg Leu Tyr Glu Gly Glu Ala Asp Ile Met
145                 150                 155                 160

Ile Ser Phe Ala Val Arg Glu His Gly Asp Phe Tyr Pro Phe Asp Gly
                165                 170                 175

Pro Gly Asn Val Leu Ala His Ala Tyr Ala Pro Gly Pro Gly Ile Asn
            180                 185                 190

Gly Asp Ala His Phe Asp Asp Asp Glu Gln Trp Thr Lys Asp Thr Thr
        195                 200                 205

Gly Thr Asn Leu Phe Leu Val Ala Ala His Glu Ile Gly His Ser Leu
    210                 215                 220
```

Gly Leu Phe His Ser Ala Asn Thr Glu Ala Leu Met Tyr Pro Leu Tyr
225                 230                 235                 240

His Ser Leu Thr Asp Leu Thr Arg Phe Arg Leu Ser Gln Asp Asp Ile
                245                 250                 255

Asn Gly Ile Gln Ser Leu Tyr Gly Pro Pro Asp Ser Pro Glu Thr
            260                 265                 270

Pro Leu Val Pro Thr Glu Pro Val Pro Glu Pro Gly Thr Pro Ala
        275                 280                 285

Asn Cys Asp Pro Ala Leu Ser Phe Asp Ala Val Ser Thr Leu Arg Gly
        290                 295                 300

Glu Ile Leu Ile Phe Lys Asp Arg His Phe Trp Arg Lys Ser Leu Arg
305                 310                 315                 320

Lys Leu Glu Pro Glu Leu His Leu Ile Ser Ser Phe Trp Pro Ser Leu
                325                 330                 335

Pro Ser Gly Val Asp Ala Ala Tyr Glu Val Thr Ser Lys Asp Leu Val
            340                 345                 350

Phe Ile Phe Lys Gly Asn Gln Phe Trp Ala Ile Arg Gly Asn Glu Val
        355                 360                 365

Arg Ala Gly Tyr Pro Arg Gly Ile His Thr Leu Gly Phe Pro Pro Thr
370                 375                 380

Val Arg Lys Ile Asp Ala Ala Ile Ser Asp Lys Glu Lys Asn Lys Thr
385                 390                 395                 400

Tyr Phe Phe Val Glu Asp Lys Tyr Trp Arg Phe Asp Glu Lys Arg Asn
                405                 410                 415

Ser Met Glu Pro Gly Phe Pro Lys Gln Ile Ala Glu Asp Phe Pro Gly
            420                 425                 430

Ile Asp Ser Lys Ile Asp Ala Val Phe Glu Glu Phe Gly Phe Phe Tyr
        435                 440                 445

Phe Phe Thr Gly Ser Ser Gln Leu Glu Phe Asp Pro Asn Ala Lys Lys
    450                 455                 460

Val Thr His Thr Leu Lys Ser Asn Ser Trp Leu Asn Cys
465                 470                 475

<210> SEQ ID NO 7
<211> LENGTH: 707
<212> TYPE: PRT
<213> ORGANISM: Homo Sapiens
<220> FEATURE:
<221> NAME/KEY: MISC_FEATURE
<223> OTHER INFORMATION: MMP9 Homo Sapiens

<400> SEQUENCE: 7

Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
                20                  25                  30

Gly Asp Leu Arg Thr Asn Leu Thr Asp Arg Gln Leu Ala Glu Glu Tyr
            35                  40                  45

Leu Tyr Arg Tyr Gly Tyr Thr Arg Val Ala Glu Met Arg Gly Glu Ser
        50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly

-continued

```
                100                 105                 110
Asp Leu Lys Trp His His His Asn Ile Thr Tyr Trp Ile Gln Asn Tyr
        115                 120                 125
Ser Glu Asp Leu Pro Arg Ala Val Ile Asp Ala Phe Ala Arg Ala
        130                 135             140
Phe Ala Leu Trp Ser Ala Val Thr Pro Leu Thr Phe Thr Arg Val Tyr
145                 150                 155                 160
Ser Arg Asp Ala Asp Ile Val Ile Gln Phe Gly Val Ala Glu His Gly
                165                 170                 175
Asp Gly Tyr Pro Phe Asp Gly Lys Asp Gly Leu Leu Ala His Ala Phe
            180                 185                 190
Pro Pro Gly Pro Gly Ile Gln Gly Asp Ala His Phe Asp Asp Asp Glu
        195                 200                 205
Leu Trp Ser Leu Gly Lys Gly Val Val Val Pro Thr Arg Phe Gly Asn
        210                 215                 220
Ala Asp Gly Ala Ala Cys His Phe Pro Phe Ile Phe Glu Gly Arg Ser
225                 230                 235                 240
Tyr Ser Ala Cys Thr Thr Asp Gly Arg Ser Asp Gly Leu Pro Trp Cys
                245                 250                 255
Ser Thr Thr Ala Asn Tyr Asp Thr Asp Asp Arg Phe Gly Phe Cys Pro
            260                 265                 270
Ser Glu Arg Leu Tyr Thr Gln Asp Gly Asn Ala Asp Gly Lys Pro Cys
        275                 280                 285
Gln Phe Pro Phe Ile Phe Gln Gly Gln Ser Tyr Ser Ala Cys Thr Thr
        290                 295                 300
Asp Gly Arg Ser Asp Gly Tyr Arg Trp Cys Ala Thr Thr Ala Asn Tyr
305                 310                 315                 320
Asp Arg Asp Lys Leu Phe Gly Phe Cys Pro Thr Arg Ala Asp Ser Thr
                325                 330                 335
Val Met Gly Gly Asn Ser Ala Gly Glu Leu Cys Val Phe Pro Phe Thr
            340                 345                 350
Phe Leu Gly Lys Glu Tyr Ser Thr Cys Thr Ser Glu Gly Arg Gly Asp
        355                 360                 365
Gly Arg Leu Trp Cys Ala Thr Thr Ser Asn Phe Asp Ser Asp Lys Lys
        370                 375                 380
Trp Gly Phe Cys Pro Asp Gln Gly Tyr Ser Leu Phe Leu Val Ala Ala
385                 390                 395                 400
His Glu Phe Gly His Ala Leu Gly Leu Asp His Ser Ser Val Pro Glu
                405                 410                 415
Ala Leu Met Tyr Pro Met Tyr Arg Phe Thr Glu Gly Pro Pro Leu His
            420                 425                 430
Lys Asp Asp Val Asn Gly Ile Arg His Leu Tyr Gly Pro Arg Pro Glu
        435                 440                 445
Pro Glu Pro Arg Pro Pro Thr Thr Thr Pro Gln Pro Thr Ala Pro
        450                 455                 460
Pro Thr Val Cys Pro Thr Gly Pro Pro Thr Val His Pro Ser Glu Arg
465                 470                 475                 480
Pro Thr Ala Gly Pro Thr Gly Pro Pro Ser Ala Gly Pro Thr Gly Pro
                485                 490                 495
Pro Thr Ala Gly Pro Ser Thr Ala Thr Thr Val Pro Leu Ser Pro Val
            500                 505                 510
Asp Asp Ala Cys Asn Val Asn Ile Phe Asp Ala Ile Ala Glu Ile Gly
        515                 520                 525
```

```
Asn Gln Leu Tyr Leu Phe Lys Asp Gly Lys Tyr Trp Arg Phe Ser Glu
        530                 535                 540
Gly Arg Gly Ser Arg Pro Gln Gly Pro Phe Leu Ile Ala Asp Lys Trp
545                 550                 555                 560
Pro Ala Leu Pro Arg Lys Leu Asp Ser Val Phe Glu Glu Arg Leu Ser
                565                 570                 575
Lys Lys Leu Phe Phe Phe Ser Gly Arg Gln Val Trp Val Tyr Thr Gly
                580                 585                 590
Ala Ser Val Leu Gly Pro Arg Arg Leu Asp Lys Leu Gly Leu Gly Ala
            595                 600                 605
Asp Val Ala Gln Val Thr Gly Ala Leu Arg Ser Gly Arg Gly Lys Met
        610                 615                 620
Leu Leu Phe Ser Gly Arg Arg Leu Trp Arg Phe Asp Val Lys Ala Gln
625                 630                 635                 640
Met Val Asp Pro Arg Ser Ala Ser Glu Val Asp Arg Met Phe Pro Gly
                645                 650                 655
Val Pro Leu Asp Thr His Asp Val Phe Gln Tyr Arg Glu Lys Ala Tyr
                660                 665                 670
Phe Cys Gln Asp Arg Phe Tyr Trp Arg Val Ser Ser Arg Ser Glu Leu
            675                 680                 685
Asn Gln Val Asp Gln Val Gly Tyr Val Thr Tyr Asp Ile Leu Gln Cys
        690                 695                 700
Pro Glu Asp
705

<210> SEQ ID NO 8
<211> LENGTH: 476
<212> TYPE: PRT
<213> ORGANISM: Homo Sapiens
<220> FEATURE:
<221> NAME/KEY: MISC_FEATURE
<223> OTHER INFORMATION: MMP10 Homo Sapiens

<400> SEQUENCE: 8

Met Met His Leu Ala Phe Leu Val Leu Leu Cys Leu Pro Val Cys Ser
1               5                   10                  15
Ala Tyr Pro Leu Ser Gly Ala Ala Lys Glu Glu Asp Ser Asn Lys Asp
            20                  25                  30
Leu Ala Gln Gln Tyr Leu Glu Lys Tyr Tyr Asn Leu Glu Lys Asp Val
        35                  40                  45
Lys Gln Phe Arg Arg Lys Asp Ser Asn Leu Ile Val Lys Lys Ile Gln
    50                  55                  60
Gly Met Gln Lys Phe Leu Gly Leu Glu Val Thr Gly Lys Leu Asp Thr
65                  70                  75                  80
Asp Thr Leu Glu Val Met Arg Lys Pro Arg Cys Gly Val Pro Asp Val
                85                  90                  95
Gly His Phe Ser Ser Phe Pro Gly Met Pro Lys Trp Arg Lys Thr His
            100                 105                 110
Leu Thr Tyr Arg Ile Val Asn Tyr Thr Pro Asp Leu Pro Arg Asp Ala
        115                 120                 125
Val Asp Ser Ala Ile Glu Lys Ala Leu Lys Val Trp Glu Glu Val Thr
    130                 135                 140
Pro Leu Thr Phe Ser Arg Leu Tyr Glu Gly Glu Ala Asp Ile Met Ile
145                 150                 155                 160
Ser Phe Ala Val Lys Glu His Gly Asp Phe Tyr Ser Phe Asp Gly Pro
```

165                 170                 175
Gly His Ser Leu Ala His Ala Tyr Pro Pro Gly Pro Gly Leu Tyr Gly
                180                 185                 190

Asp Ile His Phe Asp Asp Glu Lys Trp Thr Glu Asp Ala Ser Gly
            195                 200                 205

Thr Asn Leu Phe Leu Val Ala His Glu Leu Gly His Ser Leu Gly
210                 215                 220

Leu Phe His Ser Ala Asn Thr Glu Ala Leu Met Tyr Pro Leu Tyr Asn
225                 230                 235                 240

Ser Phe Thr Glu Leu Ala Gln Phe Arg Leu Ser Gln Asp Asp Val Asn
                245                 250                 255

Gly Ile Gln Ser Leu Tyr Gly Pro Pro Ala Ser Thr Glu Glu Pro
            260                 265                 270

Leu Val Pro Thr Lys Ser Val Pro Ser Gly Ser Glu Met Pro Ala Lys
                275                 280                 285

Cys Asp Pro Ala Leu Ser Phe Asp Ala Ile Ser Thr Leu Arg Gly Glu
            290                 295                 300

Tyr Leu Phe Phe Lys Asp Arg Tyr Phe Trp Arg Arg Ser His Trp Asn
305                 310                 315                 320

Pro Glu Pro Glu Phe His Leu Ile Ser Ala Phe Trp Pro Ser Leu Pro
                325                 330                 335

Ser Tyr Leu Asp Ala Ala Tyr Glu Val Asn Ser Arg Asp Thr Val Phe
            340                 345                 350

Ile Phe Lys Gly Asn Glu Phe Trp Ala Ile Arg Gly Asn Glu Val Gln
                355                 360                 365

Ala Gly Tyr Pro Arg Gly Ile His Thr Leu Gly Phe Pro Pro Thr Ile
370                 375                 380

Arg Lys Ile Asp Ala Ala Val Ser Asp Lys Glu Lys Lys Lys Thr Tyr
385                 390                 395                 400

Phe Phe Ala Ala Asp Lys Tyr Trp Arg Phe Asp Glu Asn Ser Gln Ser
                405                 410                 415

Met Glu Gln Gly Phe Pro Arg Leu Ile Ala Asp Asp Phe Pro Gly Val
            420                 425                 430

Glu Pro Lys Val Asp Ala Val Leu Gln Ala Phe Gly Phe Phe Tyr Phe
                435                 440                 445

Phe Ser Gly Ser Ser Gln Phe Glu Phe Asp Pro Asn Ala Arg Met Val
            450                 455                 460

Thr His Ile Leu Lys Ser Asn Ser Trp Leu His Cys
465                 470                 475

<210> SEQ ID NO 9
<211> LENGTH: 470
<212> TYPE: PRT
<213> ORGANISM: Homo Sapiens
<220> FEATURE:
<221> NAME/KEY: MISC_FEATURE
<223> OTHER INFORMATION: MMP12 Homo Sapiens

<400> SEQUENCE: 9

Met Lys Phe Leu Leu Ile Leu Leu Leu Gln Ala Thr Ala Ser Gly Ala
1               5                   10                  15

Leu Pro Leu Asn Ser Ser Thr Ser Leu Glu Lys Asn Asn Val Leu Phe
                20                  25                  30

Gly Glu Arg Tyr Leu Glu Lys Phe Tyr Gly Leu Glu Ile Asn Lys Leu
            35                  40                  45

```
Pro Val Thr Lys Met Lys Tyr Ser Gly Asn Leu Met Lys Glu Lys Ile
     50                  55                  60
Gln Glu Met Gln His Phe Leu Gly Leu Lys Val Thr Gly Gln Leu Asp
 65                  70                  75                  80
Thr Ser Thr Leu Glu Met Met His Ala Pro Arg Cys Gly Val Pro Asp
                 85                  90                  95
Val His His Phe Arg Glu Met Pro Gly Gly Pro Val Trp Arg Lys His
             100                 105                 110
Tyr Ile Thr Tyr Arg Ile Asn Asn Tyr Thr Pro Asp Met Asn Arg Glu
         115                 120                 125
Asp Val Asp Tyr Ala Ile Arg Lys Ala Phe Gln Val Trp Ser Asn Val
130                 135                 140
Thr Pro Leu Lys Phe Ser Lys Ile Asn Thr Gly Met Ala Asp Ile Leu
145                 150                 155                 160
Val Val Phe Ala Arg Gly Ala His Gly Asp Phe His Ala Phe Asp Gly
                165                 170                 175
Lys Gly Gly Ile Leu Ala His Ala Phe Gly Pro Gly Ser Gly Ile Gly
             180                 185                 190
Gly Asp Ala His Phe Asp Glu Asp Glu Phe Trp Thr Thr His Ser Gly
         195                 200                 205
Gly Thr Asn Leu Phe Leu Thr Ala Val His Glu Ile Gly His Ser Leu
210                 215                 220
Gly Leu Gly His Ser Ser Asp Pro Lys Ala Val Met Phe Pro Thr Tyr
225                 230                 235                 240
Lys Tyr Val Asp Ile Asn Thr Phe Arg Leu Ser Ala Asp Asp Ile Arg
                245                 250                 255
Gly Ile Gln Ser Leu Tyr Gly Asp Pro Lys Glu Asn Gln Arg Leu Pro
             260                 265                 270
Asn Pro Asp Asn Ser Glu Pro Ala Leu Cys Asp Pro Asn Leu Ser Phe
         275                 280                 285
Asp Ala Val Thr Thr Val Gly Asn Lys Ile Phe Phe Phe Lys Asp Arg
290                 295                 300
Phe Phe Trp Leu Lys Val Ser Glu Arg Pro Lys Thr Ser Val Asn Leu
305                 310                 315                 320
Ile Ser Ser Leu Trp Pro Thr Leu Pro Ser Gly Ile Glu Ala Ala Tyr
                325                 330                 335
Glu Ile Glu Ala Arg Asn Gln Val Phe Leu Phe Lys Asp Asp Lys Tyr
             340                 345                 350
Trp Leu Ile Ser Asn Leu Arg Pro Glu Pro Asn Tyr Pro Lys Ser Ile
         355                 360                 365
His Ser Phe Gly Phe Pro Asn Phe Val Lys Lys Ile Asp Ala Ala Val
370                 375                 380
Phe Asn Pro Arg Phe Tyr Arg Thr Tyr Phe Phe Val Asp Asn Gln Tyr
385                 390                 395                 400
Trp Arg Tyr Asp Glu Arg Arg Gln Met Met Asp Pro Gly Tyr Pro Lys
                405                 410                 415
Leu Ile Thr Lys Asn Phe Gln Gly Ile Gly Pro Lys Ile Asp Ala Val
             420                 425                 430
Phe Tyr Ser Lys Asn Lys Tyr Tyr Tyr Phe Phe Gln Gly Ser Asn Gln
         435                 440                 445
```

```
Phe Glu Tyr Asp Phe Leu Leu Gln Arg Ile Thr Lys Thr Leu Lys Ser
    450                 455                 460

Asn Ser Trp Phe Gly Cys
465             470
```